US005498734A

United States Patent [19]
Rieke

[11] Patent Number: 5,498,734
[45] Date of Patent: *Mar. 12, 1996

[54] PREPARATION AND USE OF (2-BUTENE-1,4-DIYL)MAGNESIUM COMPLEXES IN ORGANIC SYNTHESIS

[75] Inventor: Reuben D. Rieke, Lincoln, Nebr.

[73] Assignee: University of Nebraska, Lincoln, Nebr.

[*] Notice: The term of this patent shall not extend beyond the expiration date of Pat. No. 5,231,205.

[21] Appl. No.: 100,058

[22] Filed: Jul. 30, 1993

Related U.S. Application Data

[63] Continuation-in-part of Ser. No. 949,064, Sep. 22, 1992, abandoned, which is a continuation-in-part of Ser. No. 763,629, Sep. 23, 1991, Pat. No. 5,231,205.

[51] Int. Cl.$^6$ .............................. C07F 7/08; C07F 7/22; C07F 7/24; C07F 7/30
[52] U.S. Cl. .................. 556/87; 556/406; 556/449; 556/465; 556/95; 260/665 R; 585/360; 585/407; 585/361; 585/350; 568/367; 568/374; 568/376; 568/379; 568/381; 568/816; 568/819; 568/822; 568/832; 568/838; 568/839; 568/853; 568/857; 568/909.5; 564/305; 564/374; 548/408; 548/512; 548/553; 562/433; 562/435; 549/265; 549/273; 549/295; 549/283; 549/302; 549/328; 570/186
[58] Field of Search ...................... 556/406, 449, 556/465, 87, 95; 260/665 R; 585/360, 407, 361, 350; 568/367, 374, 376, 379, 381, 816, 819, 822, 832, 838, 839, 853, 857, 909.5; 564/305, 374; 548/408, 512, 553; 562/433, 435; 549/265, 273, 295, 283, 302, 328; 570/186

[56] References Cited

U.S. PATENT DOCUMENTS

| | | |
|---|---|---|
| 3,388,179 | 6/1968 | Ramsden . |
| 4,069,267 | 1/1978 | Kamienski et al. . |
| 4,087,468 | 5/1978 | Solomon . |
| 4,166,898 | 9/1979 | Kambe et al. . |
| 4,325,840 | 4/1982 | Malpass . |
| 4,396,554 | 8/1983 | Robinson et al. . |
| 4,731,203 | 3/1988 | Bogdanovic . |
| 5,211,886 | 5/1993 | Rieke . |
| 5,211,889 | 5/1993 | Rieke . |
| 5,231,205 | 7/1993 | Rieke . |

OTHER PUBLICATIONS

M. T. Arencibia et al., "Hypervalent Organoiodine Compounds: Radical Fragmentation of Oxabicyclic Hemiacetals. Convenient Synthesis of Medium-sized and Spiro Lactones", *J. Chem. Soc. Perkin Trans.*, 1, 3349–3360 (1991).
S. Akutagawa et al., "Metal–Assisted Terpenoid Synthesis. 3. A Myrcene Magnesium Compound as a New Example of an Enediylmetal System Formed from a Conjugated Diene and Its Synthetic Applications," *J. Am. Chem. Soc.*, 98, 7420–7421 (1976).
R. Baker et al., "Reaction of 'Myrcene–Magnesium' with Esters, Acetyl Chloride, and Acetic Anhydride: Formation of Cyclopentenols and Cyclopropane Derivatives," *J. C. S. Perkin I*, 1815–1818 (1976).
N. C. Barua et al., "A Convenient Synthesis of δ–Lactones", *Synthesis*, 1067–1070 (1986).
B. Bogdanovic, "Magnesium Anthracene Systems and Their Application in Synthesis and Catalysis," *Acc. Chem. Res.*, 21, 261–267 (1988).
T. P. Burns et al., "Preparation of Grignard Reagents from 3–Halo Ethers," *J. Org. Chem.*, 48, 4141–4143 (1983).
T. P. Burns et al., "Highly Reactive Magnesium and Its Application to Organic Syntheses," *J Org. Chem.*, 52, 3674–3680 (1987).
P. Cononne et al., "Reaction of Dibromoagnesio)Alkanes with Unsymmetrically Substituted Cyclic Anhydrides", *Tetrahedron Lett.*, 21, 4167–4170 (1980).
P. Cononne et al., "One–Step Spiroannelation, Synthesis of Spiro γ– and δ–Lactones", *J. Org. Chem.*, 46, 3091–3097 (1981).
J. E. Dubois et al., "Magnesiens encombres a structure cage: synthese du bromure d'adamantyl–1 magnesium," *C. R. Acad. Sci. Ser.*, 284, 145–148 (1977).
U. M. Dzemilev et al., "Synthesis and Transformations of 'Non–Grignard' Organomagnesium Reagents Obtained from 1,3–Dienes," *J. Organomet. Chem.*, 406, 1–47 (1991).
E. Erdik, "Copper(I) Catalyzed Reactions of Organolithiums and Grignard Reagents," *Tetrahedron*, 40, 641–657 (1984).
G. Erker et al., "The Remarkable Features of (η$^4$–Conjugated Diene)zirconocene and –hafnocene Complexes," *Adv. Organomet. Chem.*, 24, 1–39 (1985).

(List continued on next page.)

Primary Examiner—Paul F. Shaver
Attorney, Agent, or Firm—Merchant, Gould, Smith, Edell, Welter & Schmidt

[57] ABSTRACT

The magnesium complexes of cyclic hydrocarbons containing conjugated dienes, such as 1,2-dimethylenecycloalkanes, and 1,3-butadienes, are readily prepared in high yields using highly reactive magnesium. Reactions of these (2-butene-1,4 diyl)magnesium reagents with electrophiles such as dibromoalkanes, alkylditosylates, alkylditriflates, bromoalkylnitriles, esters, or amides serve as a convenient method for synthesizing carbocyclic systems. Significantly, carbocycles prepared by this method contain functional groups such as the exocyclic double bond or a keto group in one of the rings which could be used for further elaboration of these molecules. Furthermore, fused bicyclic systems containing a substituted five-membered ring can be conveniently prepared at high temperatures by the reactions of (2-butene-1,4-diyl)magnesium complexes with carboxylic esters or acid halides whereas low temperatures lead to regioselective synthesis of β,γ-unsaturated ketones. Additionally, γ-lactones, including spiro γ-lactones, can be easily prepared in a one pot synthesis from the reaction of (2-butene-1,4-diyl)magnesium complexes with a ketone or aldehyde and carbon dioxide. Also, δ-lactones can be easily prepared in a one pot synthesis from the reaction of (2-butene-1,4-diyl)magnesium complexes with epoxides followed by reaction with $CO_2$. Use of α-hydroxy epoxides without the addition of $CO_2$ leads to the synthesis of vicinal diols. Chiral epoxides lead to chiral alcohols.

28 Claims, No Drawings

OTHER PUBLICATIONS

C. J. Francis et al., "Preparations of Chiral δ–Lactones via Enantiotopically Specific Pig Liver Esterase–catalyzed Hydrolyses of 3–Substituted Glutaric Acid Diesters", *J. Chem. Soc., Chem. Commun.*, 579–580 (1984).P. K. Freeman et al., "Magnesium Anthracene Dianion," *J. Org. Chem.*, 48, 879–881 (1983).

K. Fujita et al., "Magnesium–Butadiene Addition Compounds: Isolation, Structural Analysis and Chemical Reactivity," *J. Organomet. Chem.*, 113, 201–213 (1976).

B. H. Han, "Organic Sonochemistry. Ultrasound Acceleration of the Preparation of Highly Active Mg and Zn Powders," *J. Korean Chem. Soc.*, 29, 557–558 (1985).

S. Harvey et al., "Main Group Conjugated Organic Anion Chemistry. 3. Application of Magnesium–Anthracene Compounds in the Synthesis of Grignard Reagents," *J. Org. Chem.*, 53, 3134–3140 (1988).

S. Harvey, et al., "Polymer Supported 'Magnesium(anthracene)': Effective in Forming Benzylic Grignard Reagents (via Electron Transfer Reactions)," *J. C. S., Chem. Commun.*, 652–653 (1988).

Y. Kai et al., "The X–Ray Structure of a Magnesium–1, 3–Diene Complex, The Unique Mode of Coordination of Diene Observed in Penta–Coordinated Mg(THF)$_3$(s–cis–PhCH=CH–CH=CHPh)," *Chem. Lett.*, 1277–1280 (1982).

S. Kano et al., "A Synthesis of γ-Butyrolactone and Related Compounds", *Heterocycles*, 14, 661–711 (1980).

D. W. Knight, "Saturated Carbocyclic Ring Synthesis," *Gen. Synth. Methods*, 6, 277–311 (1983).

K. Kobayashi et al., "A New Route to γ–Substituted γ–Lactones and δ–Substituted δ–Lactones Based on the Regioselective β–Scission of Alkoxyl Radicals Generated from Transannular Hemiacetals", *Tetrahedron*, 47, 7245–7258 (1991).

N. A. Le et al., "Reaction of Photochemically Generated Dibromocarbene with 1,2–Dimethylenecycloalkanes. 1,4 Addition is Real", *J. Am. Chem. Soc.*, 111, 8491–8493 (1989).

W. E. Lindsell, "Magnesium, Calcium, Strontium and Barium," *Comprehensive Organometallic Chemistry*, Ch. 4.1 and 4.2; Wilkinson, Stone & Abel, ed.; Pergamon Press, Oxford (1982); pp. 155–252.

B. H. Lipshutz et al., "Reactions of Stoichiometric Higher Order, Mixed Lithio Magnesio Organocuprates," *Tetrahedron*, 42, 2873–2879 (1986).

R. M. Magid, "Nucleophilic and Organometallic Displacement Reactions of Allylic Compounds: Stereo– and Regiochemistry," *Tetrahedron*, 36, 1901–1930 (1980).

G. D. Maio et al., "δ–Lactones from δ–Ketoesters—II", *Tetrahedron*, 40, 749–755 (1984).

P. Markov et al., "Uber die Reduktion des Naphthalins mit Magnesium in Flüssigem Ammoniak," *Liebigs Ann. Chem.*, 704, 126–132 (1967).

P. Markov et al., "Reactions of Calcium and Magnesium Naphthalenides with Ethyl Esters of 2–Bromopropionic and 2–Bromobutyric Acid in Liquid Ammonia," *J. Organomet. Chem.*, 81, 1–6 (1974).

P. Markov et al., "Uber die Reaktion von Biphenyl mit Magnesium in flüssigem Ammoniak," *Monatshefte für Chemie*, 107, 619–624 (1976) (with English language abstract).

K. Mori et al., "Synthesis of Optically Active Pheromones", *Tetrahedron*, 45, 3233–3298 (1989).

S.–I. Murahashi et al., "Ruthenium–Catalyzed Oxidative Transformation of Alcohols and Aldehydes to Esters and Lactones", *J. Org. Chem.*, 52, 4319–4327 (1987).

Y. Nakano et al., "On the Reaction Between Magnesium and Iosprene," *Tetrahedron Lett.*, 28, 2833–2836 (1972).

E. Negishi, "Bimetallic Catalytic Systems Containing Ti, Zr, Ni, and Pd. Their Applications to Selective Organic Synthesis," *Pure & Appl. Chem.*, 53, 2333–2356 (1981).

D. J. Ramon et al., "Direct Synthesis of δ–Lactones from 2–(3–lithiopropyl)–1,3–Dioxolane and Carbonyl Compounds", *Tetrahedron Lett.*, 31, 3767–3770 (1990).

C. L. Raston et al., "Magnesium Anthracene: An Alternative to magnesium in the High Yield Synthesis of Grignard Reagents," *J. Chem. Soc., Chem. Commun.*, 1702–1703 (1984).

R. Rathore et al., "Substituent Directed Oxidative Cyclization with Cetyltrimethylammonium Permanganate: A General Approach to the Synthesis of γ– and δ–Lactones", *Tetrahedron Lett.*, 27, 4079–4082 (1986).

W. J. Richter, "Diorganosilacyclopent–3–ene Derivatives from Diorganodichlorosilanes and Butadienemagnesium: Evidence for Crotyl–Grignard Intermediates," *J. Organomet. Chem.*, 289, 45–49 (1985).

R. D. Rieke, "New synthetic methods using highly reactive metals," Abstract of National Institute of Health Grant No. GM35153.

R. D. Rieke et al., "Activated Metals. I. Preparation of Highly Reactive Magnesium Metal," *J. Am. Chem. Soc.*, 94, 7178–7179 (1972).

R. D. Rieke et al., "Activated Metals. The Effect of Added Metal Salts on Magnesium Reactivity," *J. C. S. Chem. Comm.*, 879–880 (1973).

R. D. Rieke et al., "Activated Metals. IV. Preparation and Reactions of Highly Reactive Magnesium Metal," *J. Am. Chem. Soc.*, 96, 1775–1781 (1974).

R. D. Rieke, "Use of Activated Metals in Organic and Organometallic Synthesis," *Top. Curr. Chem.*, 59, 1–31 (1975).

R. D. Rieke, "Preparation of Highly Reactive Metal Powders and Their Use in Organic and Organometallic Synthesis," *Acc. Chem. Res.*, 10, 301–306 (1977).

R. D. Rieke, "Preparation and Study of Highly Reactive Metal Powders," *U.S. NTIS, AD Rep.*, No.: AD–A150026, pp. 1–18 (1978) (Citation: Gov. Rep. Announce. Index (U.S.) 1978, 78(1), 171).

R. D. Rieke et al., "Highly Reactive Magnesium for the Preparation of Grignard Reagents: 1–Norbornanecarboxylic Acid," *Organic Syntheses*, 59, 85–94 (1980).

R. D. Rieke, "Studies on Unusually Reactive Metal Powders. Preparation of New Organometallic and Organic Compounds Including Potential New Catalysts," *Report*, No.: DOE/ER/10603–T3; Order No. DE85014844, 18 pp. (1985) (Citation: Energy Res. Abstr. (1985) 10(18), Abstr. No. 37255).

R. D. Rieke et al., "Preparation of Highly Reactive Metal Powders. A New Procedure for the Preparation of Highly Reactive Zinc and Magnesium Metal Powders," *J. Org. Chem.*, 46, 4323–4324 (1981).

R. D. Rieke et al., "Preparation of Highly Reactive Metal Powders" Some of Their Uses in Organic and Organometallic Synthesis, *ACS Symposium Series*, 333, 223–245 (1987).

R. D. Rieke, "Preparation of Organometallic Compounds from Highly Reactive Metal Powders," *Science*, 246, 1260–1264 (1989).

R. D. Rieke et al., "New Organocopper Reagents Prepared

Utilizing Highly Reactive Copper," *Tetrahedron*, 45, 443–454 (1989).

R. D. Rieke, "Preparation of Highly Reactive Powders/Surfaces and Their Use in the Preparation of Organometallic Compounds," *Crit. Rev. Surf. Chem.*, 1, 131–166 (1991).

R. D. Rieke et al., "Chemistry of Substituted (2–Butene–1, 4–diyl)magnesium: A Facile Approach to Complex Carbocycles, Functionalized Ketones and Alcohols, and Silicon–Containing Heterocycles," *J. Org. Chem.*, 56, 3109–3118 (1991).

R. D. Rieke et al., "One–Step Spiroannulation Using 1,2–Bis(methylene)cycloalkane–Magnesium Reagents," *J. Org. Chem.*, 57, 6560–6565 (1992).

R. G. Salomon, "A Facile One–Step Synthesis of 5–Silaspiro[4.4]nona–2,7–diene," *J. Org. Chem.*, 39, 3602 (1974).

L. Set et al., "Synthesis of Spiro–Compounds: Use of Diselenoacetals for Generation of Quaternary Centres by Alkylation and Radical Cyclization", *J. Chem. Soc., Chem. Commun.*, 1205–1207 (1985).

K. Sugahara et al., "A Convenient Lactonization of 2– and 3–Cyclopropylalkanoic Acids to γ– and δ–Lactones", *Synthesis*, 783–784 (1990).

C. M. Thompson, "'Remote' Dianions—I. Utility of 4–Phenylsulfonylbutanoic Acid in the Mild Conversion of Aldehydes and Ketones to Lactones", *Tetrahedron Lett.*, 28, 4243–4246 (1987).

M. Vandewalle et al., "Total Synthesis of Polycarbocyclic Sesquiterpenes," *Tetrahedron*, 41, 1767–1831 (1985).

D. Walther et al., "Neue Bausteine metallorganischer Synthesen: 'Magnesium–dien'–Vergindungen," *Naturwiss. Reihe.*, 34, 789 (1985) with English language abstract D. Walther et al., New synthons for organometallic synthesis: magnesium–diene compounds, *Chem. Abs.*, 105, 746 (Abstract No. 105:42862z) (1986).

P. A. Wender et al., "Organobis(cuprates): A New Class of Reagents and Method for Spiroannelation," *J. Am. Chem. Soc.*, 110, 2218–2223 (1988).

T.–C. Wu et al., "Organocalcium Chemistry: Preparation and Reactions of Highly Reactive Calcium," *J. Org. Chem.*, 55, 5045–5051 (1990).

H. Xiong et al., "Facile Formation of Substituted 2–Butene–1,4–diylmagnesium Using Highly Reactive Magnesium: A Simple Approach to Complex Carbocycles and Functionalized Ketones," *J. Org. Chem.*, 54, 3247–3252 (1989).

H. Xiong et al., "The Magnesium Complexes of 1,2–Dimethylenecycloalkanes: A New Method for a One–Step Spiroannelation," *Tetrahedron Lett.*, 32, 5269–5272 (1991).

H. Xiong et al., "Synthesis of Spiro γ–Lactones from Conjugated Dienes", *J. Org. Chem.*, 57, 7007–7008 (1992).

H. Xiong et al., "Reactions of Magnesium Complexes of 1,2–Bis(methylene)cycloalkanes with Carboxylic Esters: The Formation of a Versatile Intermediate Capable of Generating Fused Rings or β,γ–Unsaturated Ketones," *J. Am. Chem. Soc.*, 114, 4415–4417 (1992).

M. Yamaguchi et al., "A New Synthesis of δ–Lactones from Oxetanes", *Tetrahedron Lett.*, 25, 1159–1162 (1984).M. Yang et al., "The Preparation and Some Reactions of Isoprene–Magnesium Compound," *Tetrahedron Lett.*, 44, 3843–3846 (1970).

H. Yasuda et al., "Unique Chemical Behavior and Bonding of Early– Transition–Metal–Diene Complexes," *Acc. Chem. Res.* 18, 120–126 (1985).

H. Yasuda et al., "New Aspects of Carbanion Chemistry. Structure of Pentadienyl Anions and Butenediyl Dianions and Their Roles in Organic and Inorganic Syntheses," *Recent Advances in Anionic Polymerization*, 59–71 (1987).

S. H. Yu et al., "Preparation of Alkylmagnesium Fluorides," *J. Org. Chem.*, 36, 2123–2128 (1971).

H. Xiong, "Chemistry of Conjugated Diene–Magnesium Reagents: A Novel Approach to Cyclic and Functionalized Molecules," Ph.D. Thesis, The University of Nebraska—Lincoln (1992).

PREPARATION AND USE OF (2-BUTENE-1,4-DIYL)MAGNESIUM COMPLEXES IN ORGANIC SYNTHESIS

GOVERNMENT SUPPORT

The present invention was made with government support under Grant No. GM35153 awarded by the National Institute of Health. The Government has certain rights in this invention.

CROSS REFERENCE TO RELATED APPLICATION

This application is a continuation-in-part of application Ser. No. 07/949,064 filed Sep. 22, 1992; now abandoned, which is a continuation-in-part of application Ser. No. 07/763,629, filed Sep. 23, 1991, now U.S. Pat. No. 5,231,205 both of which are incorporated herein by reference.

BACKGROUND OF THE INVENTION

Metallic magnesium reacts with certain 1,3-dienes yielding halide-free organomagnesium compounds. These reactions are typically catalyzed by alkyl halides or transition metal salts. The dienemagnesium compounds produced from these reactions have been mainly limited to open-chain 1,3-dienes, including 1,3-butadiene, 2-methyl-1,3-butadiene, i.e., isoprene, 1-methyl-3-methylene-1,6-octadiene, i.e., myrcene, 2,3-dimethyl-l,3-butadiene, and (E,E)-1,4-diphenyl-1,3-butadiene.

There are problems associated with the preparation of these reagents using metallic magnesium, however. For example, the reaction of metallic magnesium with 1,3-dienes such as 1,3-butadiene or isoprene usually involves dimerization, trimerization, or oligomerization of the product. Furthermore, the reactions are generally accompanied by a variety of by-products. Consequently, the utilization of these reagents in organic synthesis has been quite limited, except for perhaps the use of 1,3-butadiene-magnesium in organometallic synthesis.

It has recently been demonstrated that substituted (2-butene-1,4-diyl)magnesium complexes can be prepared using highly reactive magnesium and 1,4-diphenyl-1,3-butadiene or 2,3-dimethyl-1,3-butadiene. The highly reactive magnesium is produced from $MgCl_2$, Li, and naphthalene in tetrahydrofuran. The substituted (2-butene-1,4-diyl) magnesium complexes produced are halide-free organomagnesium reagents, i.e., bis-Grignard reagents, containing two formal Mg-C bonds in one organic species. They have been shown to function as bisnucleophiles in reactions with electrophiles. For example, these bis-Grignard reagents formed from 1,3-butadienes react with αω-alkylene dihalides in either 1,2-, 1,4-, or 2,1- additions to give complex carbocycles.

Although reactions of highly reactive magnesium with symmetrical 1,3-dienes, specifically, 1,4-diphenyl-1,3-butadiene and 2,3-dimethyl-1,3-butadiene, have been shown, reactions with more complex 1,3-dienes have not been discussed to any significant extent in the literature. Thus, it is an object of this invention to prepare (2-butene-1,4-diyl)magnesium complexes from more complex 1,3-diene systems than simple symmetrical 1,3-butadienes such as 1,4-diphenyl-1,3-butadiene and 2,3-dimethyl-1,3-butadiene. Furthermore, it is an object of this invention to utilize such (2-butene-1,4-diyl)magnesium complexes in the synthesis of new organic compounds or the synthesis of known organic compounds using more effective and/or more direct synthetic methods. It is also an object of the present invention to utilize the organomagnesium reagents produced from 1,3-dienes in the preparation of complex organic molecules.

SUMMARY OF THE INVENTION

The present invention is directed to a method for the preparation of carbocycles, spiroheterocycles such as silicon-containing spiroheterocycles, γ-lactones including spiro γ-lactones, δ-lactones including spiro δ-lactones, γ-lactams, amines, amino acids, and alcohols including chiral vicinal diols. Herein, carbocycles refer to cyclic carbon-containing molecules. This includes spirocycles and fused-ring hydrocarbon systems. Herein, spirocycles refer to molecular structures with two rings having one atom in common. This atom is typically a carbon atom; however, for the silicon-containing spiroheterocycles, for example, this atom is a silicon atom.

The method of preparing carbocycles consists of: contacting a magnesium(II) salt in an ethereal, polyethereal, or hydrocarbon solvent, preferably an ethereal or polyethereal solvent, and more preferably tetrahydrofuran, with a reducing agent having a reduction potential of about −1.5 volts, or more negative, relative to standard calomel electrode (SCE), to form a highly reactive magnesium species; contacting the highly reactive magnesium species with a cyclic hydrocarbon containing at least two conjugated exocyclic double bonds to form a (2-butene-1,4-diyl)magnesium complex; and contacting the (2-butene-1,4-diyl)magnesium complex with an electrophile to form a carbocycle. The carbocycles formed are preferably spirocycles, fused ring carbocyclic alcohols, βγ-unsaturated ketones, γ-lactones, including spiro γ-lactones, δ-lactones, including spiro δ-lactones, and γ-lactams. Other compounds can also be formed with or without any cyclic hydrocarbons therein, such as alcohols, including chiral vicinal diols, amines and amino acids.

The reducing agent used in the step of forming the highly reactive magnesium species is preferably an alkali metal salt, i.e., Li, Na, K, Rb, Cs, of an aromatic anion. More preferably, the reducing agent is selected form the group consisting of sodium naphthalenide, sodium anthracenide, sodium biphenylide, lithium naphthalenide, lithium anthracenide, lithium biphenylide, potassium naphthalenide, potassium anthracenide and potassium biphenylide. Most preferably, the reducing agent is lithium naphthalenide, preferably preformed lithium naphthalenide.

The cyclic hydrocarbon is preferably a cycloalkane containing at least two conjugated exocyclic double bonds, and more preferably, a cycloalkane containing two conjugated exocyclic double bonds. More preferably, the cyclic hydrocarbon is selected from the group consisting of 1,2-dimethylenecyclohexane, 1,2-dimethylenecyclopentane, and 1,2-dimethylenecycloheptane. The step of contacting the highly reactive magnesium species with the hydrocarbon is preferably carded out in an ethereal or polyethereal solvent.

The electrophiles used in the reaction with the (2-butene-1,4-diyl)magnesium complexes to form spirocycles, i.e., spirocyclic carbocycles, are preferably selected from the group consisting of organodihalides, organoditosylates, organoditriflates, haloalkylnitriles, esters, and amides. More preferably, the electrophiles are selected from the group consisting of alkyldibromides, alkylditosylates, and bromoalkylnitriles. The step of contacting the (2-butene-1,4-diyl)magnesium complex with an electrophile to form a spirocycle is preferably carried out at a temperature below about 100° C., and in an ethereal or polyethereal solvent.

The present invention is also directed to a method for the preparation of a fused ring carbocyclic alcohol or a method for the preparation of β,γ-unsaturated ketones. The method for the preparation of a fused ring carbocyclic alcohol includes a first step of contacting the (2-butene-1,4-diyl)magnesium complex, prepared from the highly reactive magnesium and a cyclic hydrocarbon containing at least two conjugated exocyclic double bonds, with a carboxylic ester or acid halide. This step is carried out at a temperature no greater than about −10° C., preferably at about −78° C. to about −10° C., preferably in an ethereal or polyethereal solvent. If this intermediate is heated to about 25° C. or above, preferably to refluxing temperatures, the fused ring carbocyclic alcohol is formed. If, however, the intermediate is protonated at a temperature no greater than about 0° C., preferably no greater than about −10° C., and kept at this temperature, it is converted to a β,γ-unsaturated ketone.

The method for the preparation of spiroheterocycles, preferably silicon-containing spiroheterocycles, is similar to the method for the preparation of carbocycles in that a highly reactive magnesium species is initially formed. This highly reactive magnesium species is then combined with an unsymmetrical or a symmetrical 1,3-diene, preferably an unsymmetrical 1,3-diene, to form a (2-butene-1,4-diyl)magnesium complex. This complex is then combined with a tetrahalide reagent of the formula $MX_4$ (wherein M=Si, Ge, Sn, Pb and X=F, Cl, Br, I), to form a spiroheterocycle. Preferably, a silicon tetrahalide, such as $SiCl_4$, is used to form a silicon-containing spiroheterocycle.

The present invention is also directed to a method for the preparation of γ-lactones, particularly spiro γ-lactones, δ-lactones, particularly spiro δ-lactones, γ-lactams, amines, amino acids, and alcohols, including chiral vicinal diols. These compounds can be prepared from magnesium complexes of 1,3-dienes that are prepared from the highly reactive magnesium of the present invention. For example, the preparation of a γ-lactone involves: contacting a magnesium(II) salt in an ethereal, polyethereal, or hydrocarbon solvent with a reducing agent having a reduction potential of about −1.5 volts, or more negative, relative to SCE, to form a highly reactive magnesium species; contacting the highly reactive magnesium species with a conjugated diene to form a (2-butene-1,4-diyl)magnesium complex; contacting the (2-butene-1,4-diyl)magnesium complex with a ketone or aldehyde in an ethereal, polyethereal, or hydrocarbon solvent to form a 1,2-addition adduct resulting from the incorporation of one molecule of the ketone or aldehyde to the (2-butene-1,4-diyl)magnesium complex; contacting the 1,2-addition adduct with carbon dioxide to form a nucleophilic addition product; and contacting the nucleophilic addition product with an aqueous acid to form a γ-lactone, preferably a spiro γ-lactone. The conjugated diene can be a cyclic hydrocarbon containing at least two conjugated exocyclic double bonds, as discussed above, or an open-chain conjugated diene, such as 1,3-butadiene or 2,3-dimethyl-1,3-butadiene. The ketone and aldehyde can be any aryl or alkyl ketone or aldehyde including those containing heteroatoms, such as nitrogen. For example, the ketone can be any cyclic ketone such as cyclohexanone to yield a spiro γ-lactone, or it can be an acyclic ketone to yield a γ-lactone. Any alkyl or aryl aldehyde would yield a γ-lactone.

The method for the preparation of δ-lactones including spiro δ-lactones includes the steps of: contacting a magnesium(II) salt in an ethereal, polyethereal, or hydrocarbon solvent with a reducing agent having a reduction potential of about −1.5 volts, or more negative, relative to SCE, to form a highly reactive magnesium species; contacting the highly reactive magnesium species with a conjugated diene to form a (2-butene-1,4-diyl)magnesium complex; contacting the (2-butene-1,4-diyl)magnesium complex with an epoxide in an ethereal, polyethereal, or hydrocarbon solvent to form a 1,2-addition adduct resulting from the incorporation of one molecule of the epoxide to the (2-butene-1,4-diyl)magnesium complex; contacting the 1,2-addition adduct with carbon dioxide to form a nucleophilic addition product; and contacting the nucleophilic addition product with an aqueous acid. The conjugated diene can be a cyclic hydrocarbon containing at least two conjugated exocyclic double bonds, as discussed above, or an open-chain conjugated diene, such as 1,3-butadiene or 2,3-dimethyl-1,3-butadiene. The epoxide can have alkyl, aryl, or heterocyclic subsitutents about the epoxide group. Suitable epoxides include, but are not limited to, ethylene oxide, propylene oxide, t-butylene oxide, cyclohexene oxide, and styrene oxide.

The method for the preparation of γ-lactams includes the steps of contacting a magnesium(II) salt in an ethereal, polyethereal, or hydrocarbon solvent with a reducing agent having a reduction potential of about −1.5 volts, or more negative, relative to SCE, to form a highly reactive magnesium species; contacting the highly reactive magnesium species with a conjugated diene to form a (2-butene-1,4-diyl)magnesium complex; contacting the (2-butene- 1,4-diyl)magnesium complex with an imine in an ethereal, polyethereal, or hydrocarbon solvent to form a 1,2-addition adduct resulting from the incorporation of one molecule of the imine to the (2-butene-1,4-diyl)magnesium complex; contacting the 1,2-addition adduct with carbon dioxide at a temperature of about −78° C. to about 30° C. to form a nucleophilic addition product; contacting the nucleophilic addition product with an aqueous acid; and warming the reaction mixture to a temperature greater than about 30° C. to form a γ-lactam. The conjugated diene can be a cyclic hydrocarbon containing at least two conjugated exocyclic double bonds, as discussed above, or an open-chain diene, such as 1,3-butadiene or 2,3-dimethyl-1,3-butadiene.

Amines can be obtained following a slightly modified reaction protocol. Initial treatment of the (2-butene-1,4-diyl)magnesium complexes with an imine yields the corresponding 1,2-addition adduct. At this point, protonation of the 1,2-addition adduct will result in the formation of primary and secondary amines.

Naturally occurring and synthetic amino acids can also be obtained following a slightly modified reaction protocol to that used for the formation of a γ-lactam. If in the method for the formation of a γ-lactam, the reaction mixture is not not heated subsequent to protonation of the product of the nucleophilic addition with $CO_2$, the amino acid can be obtained in high yield. This reaction is very general and provides a route to both naturally occurring and synthetic amino acids.

The method for the preparation of alcohols, including chiral vicinal diols includes the steps of: contacting a magnesium(II) salt in an ethereal, polyethereal, or hydrocarbon solvent with a reducing agent having a reduction potential of about −1.5 volts, or more negative, relative to SCE, to form a highly reactive magnesium species; contacting the highly reactive magnesium species with a conjugated diene to form a (2-butene-1,4-diyl)magnesium complex; contacting the (2-butene-1,4-diyl)magnesium complex with an epoxide in an ethereal, polyethereal, or hydrocarbon solvent to form a 1,2-addition adduct resulting from the incorporation of one molecule of the epoxide to the (2-butene-1,4-diyl)magnesium complex; contacting the 1,2-addition adduct with a proton source, e.g. and aqueous acid, to form an alcohol. The incorporation of a chiral epoxide results in the formation of a chiral alcohol. Furthermore, incorporation of an epoxide with an α-hydroxy group will result in the formation of a vicinal diol containing a quaternary carbon center. The conjugated diene can be a cyclic hydrocarbon containing at least two conjugated exocyclic double bonds, as discussed above, or an open chain conjugated diene, such as 1,3-butadiene or 2,3-dimethyl-1,3-butadiene.

In the context of the present invention, the term "aliphatic" means a saturated or unsaturated linear, branched, or cyclic hydrocarbon radical. This term is used to encompass alkyl and vinyl radicals, for example. The term "alkyl" means a saturated linear, branched, or cyclic hydrocarbon radical. The term "heterocyclic" means a mono- or polynuclear saturated or unsaturated cyclic radical containing carbons and one or more heteroatoms such as nitrogen, oxygen, phosphorus, silicon, or sulfur or a combination thereof in the ring or rings. This includes, but is not limited to, pyridine, pyrrol, indole, thiazole, pyrazine, guanine, cytosine, thyamine, adenine, uredine, uracil, oxazole, pyrazole, hydantoin, piperazine, quinoline, xanthene, 1,10-phenanthroline, thiophene, and acridine. The term "aryl" means a mono- or polynuclear aromatic hydrocarbon radical. The term "arylalkyl" means a linear, branched, or cyclic alkyl hydrocarbon radical having a mono- or polynuclear aromatic hydrocarbon or heterocyclic substituent.

DETAILED DESCRIPTION OF THE INVENTION

The present invention is based upon the discovery that novel (2-butene-1,4-diyl)magnesium complexes can be prepared using a highly reactive magnesium metal species and symmetrical or unsymmetrical 1,3-dienes. Specifically, the invention involves a method for the formation of spirocycles, fused ring carbocyclic alcohols, β,γ-unsaturated ketones, and γ-lactones, including spiro γ-lactones, δ-lactones including spiro δ-lactones, γ-lactams, amines, amino acids, and alcohols including chiral vicinal diols, using suitable electrophiles and (2-butene-1,4-diyl)magnesium complexes prepared from either cyclic hydrocarbons containing at least two conjugated exocyclic double bonds or open-chain hydrocarbons containing at least two conjugated double bonds. Also, spiroheterocycles, such as silicon-containing spiroheterocycles, can be prepared from unsymmetrical (2-butene-1,4-diyl)magnesium complexes using a tetrahalide reagent of the formula $MX_4$ (wherein M=Si, Ge, Sn, Pb and X=F, Cl, Br, I), preferably a silicon tetrahalide. The invention also involves a method for the control of the regioselectivity of electrophilic attack of unsymmetrical (2-butene-1,4-diyl)magnesium complexes using triorganosilyl chlorides prior to reaction with a second electrophile.

The Magnesium Species

The highly reactive magnesium species of the present invention is prepared from the reduction of a substantially anhydrous magnesium(II) salt, the counterion of which can be any of a variety of anions that does not contain an acidic proton. For example, the anion can be a sulfate, nitrate, nitrite, cyanide, or halide. Preferably, the anion is a halide or cyanide. More preferably, the anion of the Mg(II) salt is Cl, F, Br, or I, and most preferably Cl.

Generally, the reducing agent can be any reducing agent that is capable of reducing Mg(II) salts in an ethereal, polyethereal, or hydrocarbon solvent. Any reducing agent having a reduction potential of about −1.5 volts or more negative, relative to the standard calomel electrode (SCE), will satisfy this relation. It is preferred, however, that the reducing agent has a reduction potential of about −1.8 volts or more negative, and most preferred that the reducing agent has a reduction potential of about −2.0 volts or more negative, relative to SCE. Examples of useable reducing agents include: alkali and alkaline earth metals; alkali and alkaline earth metal salts of aromatic anions (i.e., aromatic electron transfer compounds), such as sodium naphthalenide or lithium naphthalenide; metal hydrides, such as sodium borohydride and sodium hydride; metal intercalated graphites; and alkali metals dissolved in glymes or ethers.

Preferably, the reducing agent is an alkali metal reducing agent, such as an alkali metal, an alkali metal dissolved in glymes or ethers, or an alkali metal salt of an electron transfer compound. More preferably, the reducing agent is an alkali metal salt of an electron transfer compound, i.e., a combination of an alkali metal cation and an anion of an electron transfer compound, referred to herein as an "alkali metal complex." The electron transfer compound is preferably an aromatic electron transfer compound such as biphenyl, anthracene, or naphthalene. Examples of useful "alkali metal complex" reducing agents include, but are not limited to, complexes of an alkali metal and an aromatic electron transfer compound; alkali metal-polyether solvates; alkali metal-crown ether solvates; alkali metal-cryptate solvates, etc. Examples of a complex of an alkali metal and an aromatic electron transfer compound, i.e., aromatic anion, include sodium naphthalenide, lithium naphthalenide, sodium anthracenide, lithium anthracenide, sodium biphenylide, lithium biphenylide, and the like. Most preferably, the reducing agent is an alkali metal arene salt, i.e., a complex of an alkali metal and an aromatic electron transfer compound, the most preferred of which is lithium naphthalenide.

In certain preferred embodiments the alkali metal complex reducing agent is preformed. By "preformed" it is meant that the alkali metal and about 1.0–1.2 moles of the electron transfer compound per mole of the alkali metal, are allowed to react substantially completely, i.e., until substantially all tile alkali metal is consumed, before contacting any magnesium salts. The formation of the preformed reducing agent typically takes place in an ethereal, polyethereal, or hydrocarbon solvent, and generally is substantially complete in less than about eight hours, preferably in less than about two hours.

The highly reactive magnesium species is composed of formally zerovalent magnesium metal atoms in the form of a finely divided black powder. By "formally zerovalent" it is meant that the formal oxidation state, or charge, is equal to the group number (i.e., 2) minus the number of unshared electrons (i.e., 2) minus the number of bonds (i.e., 0). Preferably, the zerovalent highly reactive magnesium species is a mixture or combination of zerovalent magnesium metal atoms and an alkali metal salt. The alkali metal salt is preferably a salt of the counterion associated with the Mg(II) salt from which the highly reactive magnesium species was prepared.

The highly reactive magnesium powder typically settles out of solution after a few hours leaving a clear solution. The solvent can then be removed via cannula. The metal powder can then be washed to remove the electron carder as well as the alkali metal salt produced from the cation of the aromatic reducing agent and the anion of the magnesium salt starting material if so desired. Although the highly reactive magnesium is preferably washed prior to further reaction, it can contain residual alkali metal salt.

The process for reduction to produce the highly reactive magnesium species of the present invention is conducted under conditions designed to prevent its reoxidation. Generally, these conditions include use of a nonhydroxylic solvent, such as ethereal, polyethereal, or hydrocarbon solvents and the exclusion of oxygen. Preferably, these conditions include temperatures of about 100° C. or less, an inert atmosphere, e.g., an argon or nitrogen atmosphere, a reaction time of about two hours or less. More preferably, the temperature is about 80° C. or less, and most preferably the reduction of the Mg(II) salt is conducted at ambient temperatures, i.e., at about 20–30° C.

Examples of useable solvents include dimethyl ether, diethyl ether, methyl-t-butyl ether, tetrahydrofuran (THF), 1,2-dimethoxyethane (DME or glyme), diglyme, triglyme, benzene, xylene, hexanes, and the like. More preferably, the reduction of the Mg(II) salt is carried out in an ethereal or polyethereal solvent such as diethyl ether, dimethyl ether, tetrahydrofuran, and the like, and most preferably in tetrahydrofuran (THF). If a hydrocarbon solvent (e.g., benzene, xylene, hexanes, etc.) is used, it preferably contains a secondary solubilizing agent such as N,N,N',N'-tetramethylethylenediamine (TMEDA) to assist in solubilizing the starting materials. If the reducing agent is an alkali metal reducing agent, but not an alkali metal salt of an electron transfer compound, the solvent is one whose boiling point exceeds the melting point of the alkali metal.

Typically, the molar ratio of the reducing agent to the Mg(II) salt is about 2:1; however, the Mg(II) salt can be in excess. Preferably, the Mg(II) salt is present in an amount of about 0.8–1.2 moles per 1.8–2.2 moles of a one-electron reducing agent. It is often desirable, however, to use a slight excess of the magnesium salt relative to the alkali metal, to decrease the chance that the reducing agent could interfere with the subsequent use of the highly reactive magnesium.

There are several methods of preparation of the zerovalent highly reactive magnesium species of the present invention. For example, the Mg(II) salt can be prepared by the combination of an alkali metal, such as K or Na, in a solvent whose boiling point exceeds the melting point of the alkali metal, such as THF or glyme. By this, it is meant that about two moles, i.e., about 1.8–2.2 moles, of an alkali metal are used per mole of magnesium salt. This method is represented by Example 1.

Another method for the preparation of the reactive magnesium species involves a one-step reduction of a Mg(II) salt in the presence of an electron transfer compound. This method is represented by the reduction of $MgCl_2$ in Example 2. Specifically, this method includes the reduction of a Mg(II) salt in the presence of an alkali metal, such as lithium, and an effective catalytic amount of an electron transfer compound, such as the aromatic electron transfer compound naphthalene. With respect to this method, by an "effective catalytic amount" it is meant that a sufficient amount of the electron transfer compound is present to effect the reduction in less than about three hours, preferably in less than about two hours. The electron transfer compound is typically present in no greater than about 10 mole-%, preferably no greater than about 6 mole-%, and most preferably within a range of about 2 mole-% to about 5 mole-%, of the alkali metal present. The alkali metal is present in an amount of about 1.8–2.2 moles per mole of magnesium salt being reduced.

A third method for the preparation of a reactive magnesium species involves a two-step reduction of a Mg(II) salt using a preformed reducing agent. This method is represented by the reduction of $MgCl_2$ in Example 3. The magnesium salt in a solvent, e.g., $MgCl_2$ in THF, is transferred into the solution of the preformed reducing agent, e.g., lithium naphthalenide in THF. Alternatively, the preformed reducing agent can be added to the magnesium salt. The reduction of the Mg(II) salt in the second step of this two step method using a preformed reducing agent is typically carried out in less than about eight hours, preferably in less than about two hours, and more preferably in less than about one hour. Preferably, the total reaction time for both steps is less than about eight hours.

A fourth method for the preparation of a reactive magnesium species involves a two-step reduction of a Mg(II) salt in the presence of an electron transfer compound and an excess of an alkali metal. This method is represented by the reduction of $MgCl_2$ in Example 4. The reducing agent is formed from an alkali metal and an effective catalytic amount of an electron transfer compound. By an "effective catalytic amount" it is meant that a sufficient amount of the electron transfer compound is present to effect the reduction in less than about three hours, preferably in less than about two hours. Preferably, this involves the use of no greater than about 10 mole-% of the electron transfer reagent, more preferably no greater than about 6 mole-%, and most preferably within a range of about 2–5 mole-%, of the alkali metal present. The alkali metal is present in an amount of about 1.8–2.2 moles per mole of magnesium salt being reduced. Thus, a solution of the resultant alkali metal complex reducing agent, i.e., the complex of the alkali metal and electron transfer compound, contains unreacted alkali metal.

A magnesium salt, preferably a magnesium salt solution, e.g., $MgCl_2$ in THF, or a magnesium salt suspension, is then slowly transferred into the solution of the alkali metal reducing agent, e.g., lithium naphthalenide in THF, containing unreacted alkali metal, e.g., lithium. By "slowly" it is meant that the Mg(II) salt is added to the solution of the reducing agent containing unreacted alkali metal at a rate that ensures the presence of excess alkali metal complex reducing agent relative to solubilized Mg(II) salt. This is evidenced by adding the Mg(II) salt at a rate such that the color of the reducing agent solution remains dark green, if a complex of an alkali metal and aromatic electron transfer compound is used. Although not intending to be a limitation to the invention in any way, it is believed that as the reducing agent is consumed, the recovered naphthalene reacts with the unreacted lithium to form lithium naphthalenide until all the lithium is consumed. This is unexpected because the small amount of electron carrier is expected to lead to long reduction times of several hours and even days, rather than minutes. In contrast, the relatively short reduction times with small amount of electron carrier makes this an especially appealing method.

The alkali metal complex reducing agents, e.g., lithium naphthalenide, can also be generated by electrochemical reduction of an electron transfer compound, e.g., naphthalene, using an alkali metal salt, e.g., a lithium halide, as the electrolyte. That is, an alkali metal complex reducing agent can be formed electrochemically. This can be carried out in an electrochemical cell containing an ethereal or polyethereal solvent using an electrode of palladium, platinum, carbon, or gold. Useful electrodes can be in any of a variety of forms. They can be solid, porous, or in the form of a slurry. The electrochemical route is advantageous and preferred at least because it avoids the use of alkali metals, which can be quite dangerous.

As a representative example of this procedure, naphthalene can be reduced in an inert atmosphere in the presence of a lithium salt, as the electrolyte, in THF. The electrode can be a large surface area electrode to facilitate the reduction.

Once the lithium naphthalenide is formed, it can be transferred to the magnesium salt, or the magnesium salt can be transferred to it, for formation of the zerovalent highly reactive magnesium.

Although the magnesium species can be maintained for a time under an inert atmosphere and ambient temperatures, it is also quite reactive. Consequently, it is preferably synthesized and used immediately or within a very short period of time. However, it can be stored for long periods of time under an inert atmosphere.

The magnesium species of this invention will react with symmetrical and unsymmetrical 1,3-diene compounds to produce selectively reactive (2-butene-1,4-diyl)magnesium compounds. These organomagnesium species undergo a variety of reactions to produce both novel organic compounds and novel synthetic methods for known organic compounds. One type of novel (2-butene-1,4-diyl)magnesium complex results from the reaction of this highly reactive magnesium with cyclic hydrocarbons containing at least two conjugated exocyclic double bonds, such as occur in 1,2-dimethylenecyclohexane, 1,2-dimethylenecyclopentane, and 1,2-dimethylenecycloheptane, for example.

Spiroannelation

Highly reactive magnesium reacts smoothly with cyclic hydrocarbons containing at least two conjugated exocyclic double bonds to produce the corresponding (2-butene-1,4-diyl)magnesium complexes in high yield. The cyclic hydrocarbons can be any of a variety of cyclic alkanes or cyclic alkenes containing at least two conjugated exocyclic double bonds providing, however, that any double bonds in the ring are not in conjugation with the exocyclic double bonds. Preferably, these cyclic hydrocarbons do not contain any additional functional groups that react with the highly reactive magnesium preferentially to the conjugated exocyclic double bond functionalities. More preferably, the cyclic hydrocarbons are cycloalkanes containing at least two exocyclic double bonds. Most preferably, the cycloalkanes are 1,2-dimethylenecycloalkanes, such as 1,2-dimethylenecyclohexane, 1,2-dimethylenecyclopentane, and 1,2-dimethylenecycloheptane. The resulting (2-butene-1,4-diyl)magnesium complexes prepared from cyclic hydrocarbons with conjugated exocyclic double bonds react with a variety of electrophiles, i.e., compounds that are deficient in electrons, to form carbocycles, including spirocycles, i.e., structures with two rings having one carbon atom in common (Tables I and II). Spirocycles, particularly the spiro[4.5]decane and spiro[5.5]undecane ring systems, constitute the basic carbon framework found in a wide variety of naturally occurring sesquiterpenes.

The electrophiles include, but are not limited to, organodihalides, such as 1,2-dibromoethane, 1,3-dibromo-propane, 1,4-dibromobutane, and 1,5-dibromopentane, organoditosylates, such as ethylene glycol di-p-tosylate, haloalkylnitriles, such as $Br(CH_2)_nCN$ compounds wherein n=1–3, organoditriflates, esters, amides, and the like. The reactions with the electrophiles typically yield carbocycles in isolated yields greater than about 40%, and often greater than about 50%.

Significantly, a wide variety of ring sizes can be generated using this approach, making this an advantageous method for the easy preparation of a wide variety of carbocycles, particularly spirocycles. Furthermore, the spirocycles typically formed by this method contain functional groups, such as an exocyclic double bond or a keto group, in one of the rings that can be used for further elaboration of these molecules.

The reaction conditions for production of (2-butene-1,4-diyl)magnesium complexes resulting from the reaction of highly reactive magnesium with cyclic hydrocarbons having conjugated exocyclic double bonds include ambient temperatures, i.e., about 20° C. to 30° C., the absence of oxygen, and an excess of highly reactive magnesium. Generally, these conditions include use of ethereal, polyethereal, or hydrocarbon solvents. Preferably, the reactions are carried out under an inert atmosphere of argon or nitrogen with a ratio of magnesium to cyclic hydrocarbon present in a range of about 1:1 to 2:1 molar equivalents. The reaction time is preferably 3–4 hours, and the solvent is preferably an ether or polyether solvent such as diethyl ether, dimethyl ether, tetrahydrofuran, and the like. More preferably, the solvent is tetrahydrofuran.

The subsequent reactions of these (2-butene-1,4-diyl)magnesium complexes with electrophiles to produce carbocycles, particularly spirocycles include temperatures of less than about 100° C., preferably at a temperature of about −80° C. to about 80° C., and the absence of oxygen. Generally, these reactions are carried out in ethereal, polyethereal, or hydrocarbon solvents. Preferably, the reactions are carded out in tetrahydrofuran under an inert atmosphere of argon or nitrogen at a temperature of about −78° C. with subsequent warming. The keto-functionalized products also include a step whereby $H_3O^+$ is added subsequent to warming.

Fused Ring Carbocyclic Alcohols and β,γ-Unsaturated Ketones

This chemistry can also be extended to the construction of fused ring carbocycles, which are present in many naturally occurring sesquiterpenes. For example, fused carbocyclic alcohols can be obtained by the reaction of (2-butene-1,4-diyl)magnesium complexes prepared from cyclic hydrocarbons containing two conjugated exocyclic double bonds with carboxylic esters and acid halides, particularly acid chlorides. These reactions can be also used to prepare carbocycles containing a β,γ-unsaturated ketone functionality generally by controlling the reaction temperature (Table III).

This approach is of general synthetic utility for the preparation of fused carbocyclic alcohols or β,γ-unsaturated ketones depending on the reaction temperatures. That is, treatment of (2-butene-1,4-diyl)magnesium complexes, prepared as described above, with carboxylic esters or acid halides at a temperature no greater than about −10° C., preferably at a temperature of about −78° C. to about −10° C. produces an intermediate. Protonating this intermediate at a temperature no greater than about 0° C., preferably no greater than about −10°, with mineral acids, for example, results in the formation of β,γ-unsaturated ketones in isolated yields of at least about 50%. On the other hand, warming the intermediate to room temperature, i.e., 25° C., or greater, preferably up to refluxing temperatures, followed by workup and isolation affords a fused ring carbocyclic alcohol in isolated yields of at least about 50%.

The further addition of an acid halide, preferably an acid chloride, to the intermediate at a temperature below about −10° C., preferably below about −20° C., alternatively can lead to the formation of spirocyclic carbocycle containing a three-membered ring. That is, a (2-butene-1,4-diyl)magnesium complex can be combined with a carboxylic ester or a first acid halide, preferably an acid chloride, and then combined with a second acid halide, which can be the same as the first acid halide, to form a carbocyclic spirocycle containing a three-membered ring. This is represented by the third and last examples in Table III.

The reactions leading to β,γ-unsaturated ketones are typically regioselective, i.e., there is generally no double bond scrambling. This feature should provide a new entry to the regioselective synthesis of β,γ-unsaturated ketones from 1,3-dienes. Furthermore, the overall process from 1,2-dimethylenecycloalkanes to the corresponding fused carbocyclic alcohols represents a formal [4+1] annelation which serves as an easy route to the hydroindene, hydropentalene, and hydroazulene bicyclic systems.

The carboxylic esters or acid halides, particularly acid chlorides, used in these reactions can be any of a variety, such as, for example ethyl acetate, ethyl butyrate, ethyl benzoate, and acetyl chloride. These reactions can be carried out in ethereal, polyethereal, or hydrocarbon solvents. Preferably, they are carded out in the tetrahydrofuran.

Preparation of γ-Lactones Including Spiro γ-Lactones

A useful application of substituted (2-butene-1,4-diyl)magnesium complexes formed from a conjugated diene, e.g., either cyclic hydrocarbons containing at least two conjugated exocyclic double bonds or open-chain hydrocarbons containing at least two conjugated double bonds, is the novel one-pot synthesis of γ-lactones, preferably spiro γ-lactones (Table IV). The cyclic hydrocarbons useful in this synthetic method are the same as those discussed above with respect to spiroannelation. The open-chain conjugated dienes can be a variety of dienes containing at least two double bonds in conjugation, i.e., separated by a carbon-carbon single bond. Preferably, these open-chain conjugated dienes do not contain any additional functional groups that react with the highly reactive magnesium preferentially to the conjugated double bond functionalities. More preferably, the open chain conjugated dienes are 1,3-dienes. Most preferably the open chain conjugated dienes are 1,3-butadienes, such as 2,3-dimethyl-1,3-butadiene.

Spiro γ-lactones and other γ-lactones can be obtained in yields in excess of 50%, preferably in excess of 60%, by initially treating (2-butene-1,4diyl)magnesium complexes at a temperature of −90° C. to −70° C. with a ketone or aldehyde to give the corresponding 1,2-addition adduct. The ketone or aldehyde is preferably present in an amount of approximately one mole of ketone or aldehyde per mole of (2-butene-1,4-diyl)magnesium complex. The ketones can be any alkyl, aryl, or mixed alkyl-aryl ketone. Preferably, the ketone is selected from the group consisting of acetone, cyclohexanone, and cyclopentanone. The aldehydes can be any alkyl or aryl aidehyde. Preferably, the aidehyde is selected from the group consisting of benzaldehyde and acetaldehyde. It is noted that the aryl ketones and aryl aldehydes include within their scope groups containing heteroatoms such as nitrogen, for example.

Subsequent to this initial step, carbon dioxide is combined with the 1,2-addition adduct to form a nucleophilic addition product. This reaction is preferably carded out by bubbling gaseous carbon dioxide through the reaction mixture containing the 1,2-addition adduct. This nucleophilic addition product is a magnesium salt of an organic molecule containing both an alkoxy and a carboxylate group (—COO$^{31}$). The nucleophilic addition reaction with $CO_2$ preferably occurs at a temperature of about 0° C. to about 25° C. Protonation using an aqueous acid, followed by a slight warming of the reaction mixture to a temperature of about 30° C. to about 50° C. forms the γ-lactone. The aqueous acid is preferably a strong mineral, i.e., inorganic, acid. More preferably, the acid is selected from the group consisting of HCl, $H_2SO_4$, and $H_3PO_4$. Most preferably, the acid is HCl. Significantly, this approach can also be used to prepare spiro γ-lactones containing two spiro centers. The representative examples of this dispiroannelation are listed in Table IV (Entries 2 and 3).

Preparation of Spiroheterocycles

One of the useful applications of substituted (2-butene-1,4-diyl)magnesium complexes formed from unsymmetrical or symmetrical 1,3-dienes is the facile synthesis of spiroheterocyclic compounds. Significantly, double annelation can be accomplished in one step by treating symmetrical or unsymmetrical, preferably unsymmetrical, (2-butene-1,4-diyl)magnesium complexes with $MX_4$ (wherein M=Si, Ge, Sn, Pb and X=F, Cl, Br, I) to form spiroheterocycles (Table V).

Although it is particularly difficult to prepare unsymmetrical (2-butene-1,4-diyl)magnesium complexes from ordinary magnesium due to extensive polymerization, the use of highly reactive magnesium circumvents this problem. For example, an excess of newly generated highly reactive magnesium reacts with unsymmetrical 1,3-dienes, such as, for example, isoprene, myrcene, or 2-phenyl-1,3-butadiene, in an ethereal, polyethereal, or hydrocarbon solvent at room temperature in about 2 hours to give the corresponding unsymmetrical (2-butene-1,4-diyl)magnesium complexes. The reactions are preferably carded out in THF. The color of the resulting complexes varies with the diene: pale orange for isoprene; light olive for myrcene; and reddish brown for 2-phenyl-1,3-butadiene.

Typically, the reaction to form a silicon-containing spiroheterocycle involves the combination of an excess of a symmetrical or unsymmetrical, preferably unsymmetrical, 1,3-diene with a silicon tetrahalide under extremely mild conditions. Other spiroheterocycles can be obtained from the appropriate tetrahalide reagent. Examples include $SnCl_4$, $PbCl_4$, and $GeCl_4$. These would yield the corresponding Sn, Pb, and Ge spiroheterocycles, respectively.

The reaction conditions include temperatures below about 25° C., and preferably within a range of about −80° C. to about 0° C. Most preferably the reactions are carded out at about −78° C. for about 30 minutes followed by warming to 0° C. The reactions are typically carded out in an ethereal, polyethereal, or hydrocarbon solvent and in the absence of oxygen. Preferably, the reactions are carded out under an inert atmosphere such as nitrogen or argon in tetrahydrofuran.

Regioselective Reactions of Unsymmetrical (2-Butene-1,4-diyl)magnesium Reagents with Two Different Electrophiles One of the major differences in chemistry between unsymmetrical and symmetrical (2-butene-1,4-diyl)magnesium complexes originates from the fact that the former possesses four totally different reactive sites and the latter has only two nonidentical nucleophilic centers. Accordingly, the regiochemistry of electrophilic attack is one of the essential problems associated with the reactions of unsymmetrical (2-butene-1,4-diyl)magnesium complexes. Treatment of unsymmetrical (2-butene-1,4-diyl)magnesium complexes with triorganosilyl chloride followed by cyclohexanone affords a stepwise addition across a terminal double bond with high regioselectivity. The results of the regioselective reactions are summarized in Table VI.

Typically, the conditions of the regioselective reactions include temperatures below about 25° C., preferably within a range of about −80° C. and 0° C., and the absence of oxygen. The solvent is generally an ethereal, polyethereal, or hydrocarbon solvent. Preferably, the regioselective reactions are carried out with the unsymmetrical (2-butene-1,4-diyl)magnesium complex and an organosilicon reagent, such as $Me_3SiCl$, in THF at a temperature of about −80° C. to 0° C. This is followed by the addition of an excess of a second electrophile, such as cyclohexanone. Subsequently, the reaction mixture is warmed to room temperature and the products isolated. Preferably, the organisilicon reagent is a compound of the formula $R_3SiCl$ wherein $R=C_{1-C4}$ alkanes. More preferably, the organosilicon reagent is $Me_3SiCl$ and $(n-butyl)_3SiCl$.

In a typical example, it is believed that the initial attack of the complex by the organosilicon reagent determines the selectivity, which was found to be generally dependent on both the diene substrate and the initial electrophile. The reaction of (2-methyl-2-butene-1,4-diyl)magnesium with trimethylsilyl chloride resulted in initial attack at the 4 or 1-position, producing two isomers of allylic Grignards. Reports of $^1H$ NMR studies reveal that substituted allylic Grignard reagents exist as a rapidly equilibrating mixture of Z and E primary stereoisomers. Treatment of the allylic Grignards with cyclohexanone leads to overall additions across a terminal double bond.

Increasing the size of the organosilicon reagent results in increased regioselectivity. This was demonstrated by using tri(n-butyl)silyl chloride as the initial electrophile. Larger substituents at the 2-position of the diene can also increase selectivity. For example, the magnesium complex of myrcene reacted with trimethylsilyl chloride, followed by cyclohexanone, to yield 1-(2-(4-methyl-3-pentenyl)-1-trimethylsilylmethyl-2-propenyl)cyclohexanol and 1-( 1-ethenyl-5-methyl-1-trimethylsilylmethyl-4-hexenyl)cyclohexanol in a 94:6 ratio. Furthermore, a single isomer is obtained in excellent yield by replacing the first electrophile with tri(n-butyl)silyl chloride.

Preparation of δ-Lactones Including Spiro δ-Lactones

A direct one-pot process for the synthesis of spiro δ-lactones, δ-lactones, and alcohols utilizing active magnesium is also provided. This technique involves the treatment of a conjugated diene-magnesium reagent, i.e., a (2-butene-1,4-diyl)magnesium complex, with an epoxide affording an intermediate organomagnesium addition complex, i.e., a 1,2-addition adduct, derived from the incorporation of one molecule of epoxide with the diene-magnesium complex.

Upon warming, the intermediate undergoes further nucleophlic addition to carbon dioxide. After protonation and subsequent warming, a δ-lactone is afforded by the lactonization of the resulting δ-hydroxy acid.

Spiro δ-lactones and other δ-lactones can be obtained in yields in excess of 30%, preferably in excess of 50%, and most preferably in excess of 60%, by initially treating (2-butene-1,4-diyl)magnesium complexes with an epoxide to give the corresponding addition adduct. Preferably, this reaction is carried out at a temperature of about −90° C. to about −70° C. The epoxide is preferably present in an amount of approximately 1 mole of epoxide per mole of (2-butene-1,4-diyl)magnesium complex. The epoxide can have alkyl, aryl, or heterocyclic substitutients about the epoxide group. Suitable epoxides include, but are not limited to, ethylene oxide, propylene oxide, t-butylene oxide, cyclohexene oxide, and styrene oxide. Preferably, the epoxide is selected from the group consisting of ethylene oxide, propylene oxide, t-butylene oxide, and cyclohexene oxide.

Subsequent to this initial step, carbon dioxide is combined with the addition adduct to form a nucleophilic addition product. This reaction is preferably carried out by bubbling gaseous carbon dioxide through the reaction mixture containing the addition adduct. This nucleophilic addition product is a magnesium salt of a δ-hydroxy acid. The nucleophilic addition reaction with $CO_2$ preferably occurs at a temperature of about 0° C. to about 20°–30° C. Protonation using an aqueous acid, followed by a slight warming of the reaction mixture, preferably to a temperature of about 30° C. to about 50° C., forms the δ-lactone. The aqueous acid is preferably a strong mineral, i.e., inorganic acid. More preferably, the acid is selected from the group consisting HCl, $H_2SO_4$, and $H_3PO_4$. Most preferably, the acid is HCl. Significantly, this approach can also be used to prepare spiro δ-lactones containing two spiro centers.

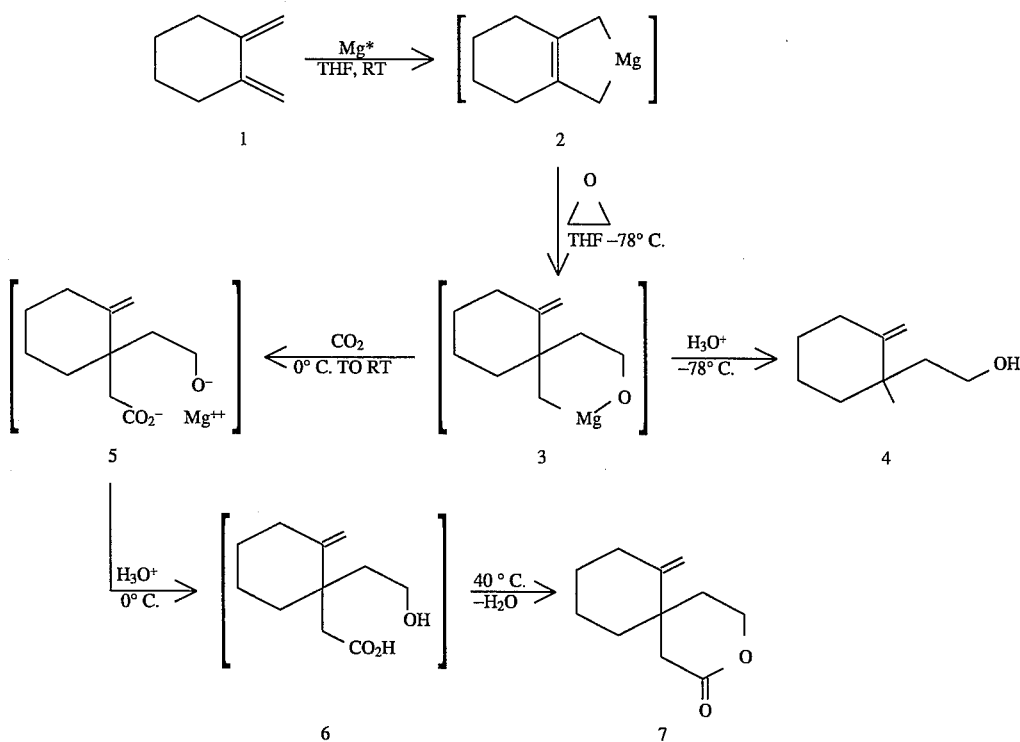

The above scheme illustrates the route for spiro δ-lactone synthesis from the magnesium complex of 1,2-bis(methylene) cyclohexane (1). Initially, treatment of 1,2-bis(methylene)cyclohexane magnesium reagent (2), i.e., (2-butene-1,4-diyl)magnesium complex, with an excess of ethylene oxide at −78° C., results in the formation of a 1,2-addition adduct (3) derived from the incorporation of one molecule of epoxide with a diene complex. Significantly, the bis-organomagnesium reactant (2) reacts with only one mole of epoxide, and preferably reacts with 100% regioselectivity in the 2-position, to give the addition adduct (3). Protonation of this adduct (3) at: −78° C. affords a primary alcohol containing a quaternary center (4). Upon warming, (3) reacts with $CO_2$ to yield the magnesium salt of a δhydroxy acid (5). Upon protonation, the δ-hydroxy acid (6) is formed which upon slight warming undergoes lactonization to yield the spiro δ-lactone (7). It is significant to note that even though (2) is treated with an excess of the epoxide, only one equivalent of the epoxide reacts with (2). Importantly, this approach can be used to prepare bicyclic spiro δ-lactones. For example, 1,2-bis(methylene)cyclohexane-magnesium reagent (2) can be treated with cyclohexene oxide at −78° C. and the reaction mixture bubbled with $CO_2$ at 0° C. with warming to room temperature.

This approach is also equally applicable to acyclic 1,3-dienes and provides a facile route to δ-lactones. The following scheme displays an outline for the synthesis of δ-lactones from (2,3-dimethyl-2-butene-1,4-diyl)magnesium (9). Reaction of cyclohexene oxide with (9) at −78° C. results in an initial attack at the 2-position of the magnesium-diene complex, affording an internal alkoxy magnesium complex (10). After gradual warming to 0° C., intermediate (10) is reacted with carbon dioxide to presumably yield the magnesium salt (11), which contains both an alkoxy and a carboxylate functional group. Upon protonation, the δ-hydroxy carboxylic acid is presumably formed and gently heated to afford a bicyclic δ-lactone (12), as a mixture of diastereomers, accommodating a quaternary center.

This methodology exhibits relatively good regioselectivity when unsymmetric epoxides are utilized as the primary electrophile. The attack of the unsymmetric epoxide occurs at the less sterically hindered carbon. Hydrolysis after treatment with 2-epoxybutane and 1,2-epoxyhexane, respectively, affords the secondary alcohols with a quaternary carbon center.

The overall procedure of the spiro δ-lactone and δ-lactone syntheses can be thought of as a molecular assembling process in which three simple independent species, i.e., a conjugated diene, an epoxide, and carbon dioxide, mediated by active magnesium are used to build a complex organic molecule in a well-controlled fashion. In the process, the construction of a quaternary carbon center and the introduction of both a hydroxyl group and a carboxyl group required for lactonization are achieved in one synthetic operation.

Preparation of δ-Lactams, Amines and Amino Acids from Conjugated Diene-Magnesium Reagents The present invention also provides a molecular assembling process in which three simple independent species, i.e., a conjugated diene, an imine, and carbon dioxide, mediated by active magnesium are utilized to construct a δ-lactams and amines in an orderly fashion. See the following reaction scheme. Also, the construction of a quaternary carbon center is generated in the process.

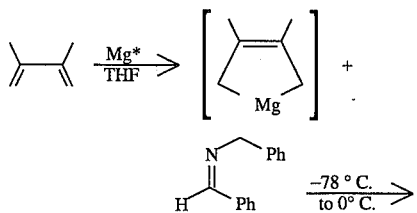

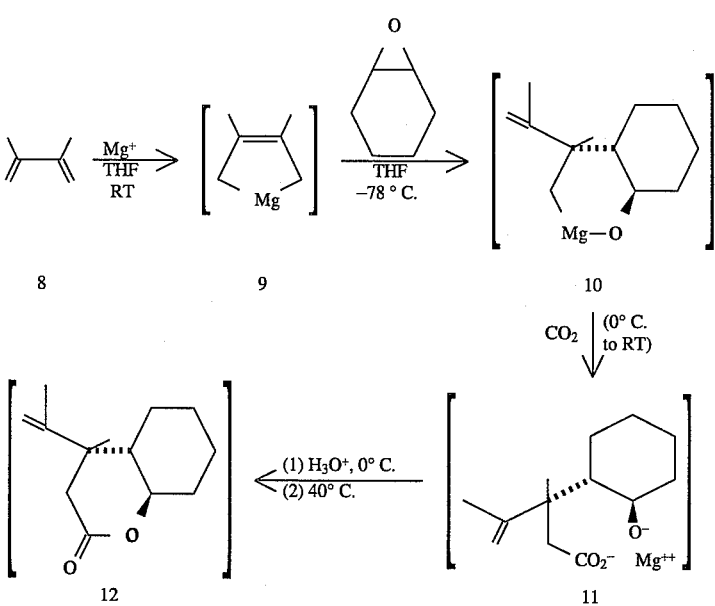

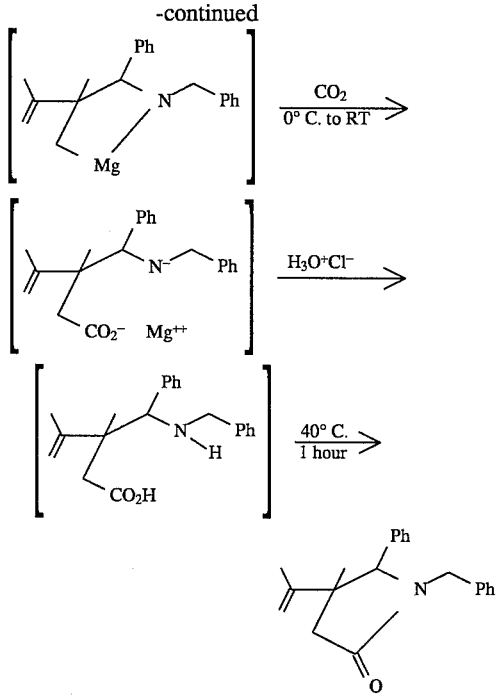

δ-Lactams can be obtained in yields in excess of 40%, preferably in excess of 60%, by initially treating (2-butene-1,4-diyl)magnesium complexes with an imine to give the corresponding 1,2-addition adduct. Preferably, this reaction is carried out at a temperature of about −90° C. to about −70° C. and subsequently allowed to warm to about 0° C. The imine is preferably present in an amount of approximately 1 mole of imine per mole of (2-butene-1,4-diyl)magnesium complex. This reaction is very general and will work with any imine according to the following formula:

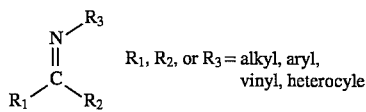

$R_1$, $R_2$, or $R_3$ = alkyl, aryl, vinyl, heterocyle

Preferably $R_1$, $R_2$, and $R_3$ are $C_{1-C100}$ alkyl, $C_5-C_{100}$ aryl, $C_2-C_{100}$ vinyl, and $C_3-C_{100}$ heterocycles. More preferably, $R_1$, $R_2$, and $R_3$ are $C_1-C_{30}$ alkyl, $C_5-C_{50}$ aryl, $C_2-C_{60}$ vinyl, and $C_3-C_{50}$ heterocycles. Examples of suitable imines include, but are not limited to, N-benzylideneaniline, benzophenone imine, acetone imine, N-benzylidenemethylamine and acetophenone imine.

Subsequent to this initial step, carbon dioxide is combined with the 1,2-addition adduct to form a nucleophilic addition product. This reaction is preferably carded out by bubbling gaseous carbon dioxide through the reaction mixture containing the 1,2-addition adduct. This nucleophilic addition product is a magnesium salt of an organic molecule containing both an amine anion and a carboxylate group (—COO$^-$). The nucleophilic addition reaction with $CO_2$ preferably occurs at a temperature of about −78° C. to about 30° C., preferably about −78° C. to about 25° C. Protonation using an aqueous acid, following by a slight warming of the reaction mixture to a temperature greater than about 30° C., preferably about 30° C. to about 50° C., forms the γ-lactam. The aqueous acid is preferably a strong mineral, i.e., inorganic acid. More preferably, the acid is selected from the group consisting HCl, $H_2SO_4$, and $H_3PO_4$. Most preferably, the acid is HCl.

Amines can be obtained following a slightly modified reaction protocol. Initial treatment of the (2-butene-1,4-diyl)magnesium complexes with an imine yields the corresponding 1,2-addition adduct. At this point, if the 1,2-addition adduct is protonated, the reaction process will result in the formation of primary and secondary amines. That is, the adduct, upon protonation, as described above, forms primary or secondary amines, if $CO_2$ is not used.

Naturally occurring and synthetic amino acids can also be obtained following a slightly modified reaction protocol to that used for the formation of a γ-lactam. If in the method for the formation of a γ-lactam, the reaction mixture is not heated subsequent to protonation of the product of the nucleophilic addition with $CO_2$, the amino acid can be obtained in high yield. That is, if the nucleophilic addition product is contacted with an aqueous acid at a temperature no greater than about 30° C., an amino acid will form. This reaction is very general and provides a route to both naturally occurring and synthetic amino acids.

Preparation of Alcohols, including Chiral Vicinal Diols

The incorporation of an unsymmetric epoxide as a primary electrophile, followed by treatment with a proton source, affords an alcohol. Incorporation of a chiral epoxide results in the formation of a chiral alcohol. Furthermore, vicinal diols with a chiral quaternary carbon center can be formed by the incorporation of an unsymmetric epoxide containing an α-hydroxyl functional group. See the following reaction scheme. It is significant to note that the 1,3-diene magnesium complex tolerates the presence of an unprotected hydroxyl group in this transformation.

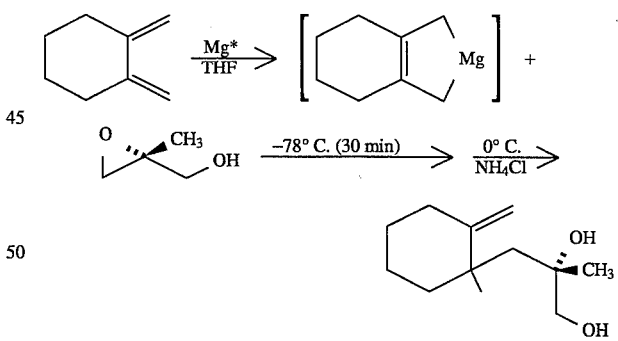

Vicinal diols can be obtained in yields in excess of 40%, preferably in excess of 60%, by initially treating (2-butene-1,4-diyl)magnesium complexes with an unsymmetrical chiral epoxide to give the corresponding epoxide ring opened addition adduct. Preferably, this reaction is carried out at a temperature of about −90° C. to about −70° C. The chiral epoxide is preferably present in an amount of approximately 1 mole of epoxide per mole of (2-butene-1,4-diyl)magnesium complex. This reaction is very general and will work with any chiral α-hydroxy epoxide of the following formula:

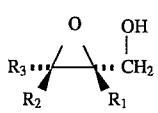

wherein $R_1$, $R_2$ and $R_3$ can be hydrogen, or any combination of hydrogen and alkyl, aryl, vinyl, or heterocyclic groups. Preferably $R_1$, $R_2$, and $R_3$ are $C_1$–$C_{100}$ alkyl, $C_5$–$C_{100}$ aryl, $C_2$–$C_{100}$ vinyl, and $C_3$–$C_{100}$ heterocycles. More preferably, $R_1$, $R_2$, and $R_3$ are $C_1$–$C_{30}$ alkyl, $C_5$–$C_{50}$ aryl, $C_2$–$C_{60}$ vinyl, and $C_3$–$C_{50}$ heterocycles. Examples of suitable chiral epoxides include, but are not limited to, R- or S- 3-hydroxy-2-methyl-1-propene oxide, R- or S- 3-hydroxy-1-methyl-1-propene oxide, R-or S- 3-hydroxy-2-ethyl-1-propene oxide, and R- or S- 3-hydroxy-2-phenyl-1-propene oxide.

Subsequent to this initial step, protonation using an aqueous acid, followed by slight warming of the reaction mixture to a temperature of about 0° C. to about 30° C. forms the vicinat diol. The aqueous acid is preferably a relatively strong mineral, i.e. inorganic, acid. More preferably, the acid is selected from the grup consisting of $NH_4Cl$, $HCl$, $H_2SO_4$, and $H_3PO_4$. Most preferably, the acid is $NH_4Cl$.

The invention will be further exemplified with respect to the various specific and preferred embodiments and techniques. It should be understood, however, that many variations and modifications may be made while remaining within the scope of the invention.

EXPERIMENTAL EXAMPLES

General Aspects $^1$H NMR (360 MHz) spectra were recorded in $CDCl_3$ solution unless specified. All chemical shifts are reported in parts per million ($\delta$) downfield from internal standard tetramethylsilane. Fully decoupled $^{13}$C NMR (50 MHz) spectra were recorded in $CDCl_3$ solution. The center peak of $CDCl_3$ (77.0 ppm) was used as the internal reference. FTIR spectra are reported in $cm^{-1}$. Mass spectra were performed by the Midwest Center for Mass Spectrometry at the University of Nebraska-Lincoln.

All manipulations were carried out under an atmosphere of argon on a dual manifold vacuum/argon system. The Linde™ prepurified grade argon was further purified by passage through a BASF™ R3–11 catalyst column at 150° C., a phosphorous pentoxide column, and a column of granular potassium hydroxide. Lithium, potassium, naphthalene, and $MgCl_2$ were weighed out and charged into reaction flasks under argon in a Vacuum Atmospheres Company dry box. Tetrahydrofuran (THF) was distilled from Na/K alloy under an atmosphere of argon immediately before use. All other reagents were used as received unless otherwise specified.

Gas chromatographic analyses were done on a Hewlett-Packard™5890A chromatograph using stainless steel columns (12 feet×⅛ inches) packed with OV-17 (3%) on 100/120 Chromosorb™ G-AW or SE-30 (5%) on 100/120 Chromosorb™ G-NAW (available from Supelco Inc.). Preparative gas chromatographic separations were obtained on a Varian Aerograph™ (model 920) chromatograph equipped with a stainless steel column (12 feet×¼ inches) packed with GP 10% SP 2100 on 100–120 Supelcoport (available from Supelco Inc.). Analytical thin-layer chromatography was performed using Merck™ 5735 indicating plates precoated with silica gel 60 $F_{254}$ (layer thickness 0.2 mm) (available from Analtech Inc.). Preparative thin-layer chromatographic separations were obtained using Anatech™ silica gel GF (layer thickness 2 mm) preparative plates (available from Analtech Inc.) or using Whatman™ PLKC 18F linear-K (layer thickness 1 mm) reversed phase preparative plates (available from Analtech Inc.). Liquid chromatographic purifications were performed by flash column chromatography using glass columns packed with Merck™ silica gel 60 (230–400 mesh) (available from Analtech Inc.). Low-temperature conditions were obtained utilizing a Neslab Endocal™ ULT-80 refrigerated circulating bath or utilizing dry ice/acetone baths.

Highly Reactive Magnesium

Highly reactive magnesium can be prepared by several acceptable methods. These methods are represented by Examples 1–4. Once the highly reactive magnesium powder was formed, it was allowed to settle. The supernatant was then drawn off, and freshly distilled THF was added, followed by the appropriate 1,3-diene. [Note: The mmoles of highly reactive magnesium refer to the theoretical amount possible, based on the original amount of magnesium chloride.]

EXAMPLE 1

PREPARATION OF HIGHLY REACTIVE MAGNESIUM FROM A MAGNESIUM HALIDE AND AN ALKALI METAL

In a typical preparation, potassium (20.8 mmol) and anhydrous magnesium chloride (10.0 mmol) in freshly distilled THF were stirred under argon for 1–2 hours at refluxing THF temperature. The reduction yielded a highly reactive finely divided black powder.

EXAMPLE 2

One-Step Reduction of a Magnesium Halide with an Alkali Metal with a Catalytic Amount of Naphthalene A predried 50mL, two-necked, round-bottomed flask was charged with lithium (30.0 mmol), a catalytic amount of naphthalene (1.6 mmol), anhydrous $MgCl_2$ (15.0 mmol), and freshly distilled THF (15 mL) in an argon atmosphere drybox. The mixture was stirred at room temperature for about 30 minutes. A highly reactive magnesium species was formed.

EXAMPLE 3

Two-Step Reduction of a Magnesium Halide with Preformed LiNp

In a typical preparation, lithium (10.0 mmol) and naphthalene (10.8 mmol) in freshly distilled THF (15 mL) were stirred under argon until the lithium was completely consumed (approximately 2 hours). The resulting dark green lithium naphthalenide was then transferred dropwise via a cannula into a THF solution (10 mL) of anhydrous magnesium chloride (4.8 mmol). The mixture was stirred at room temperature for 30 minutes. The newly formed magnesium slurry was allowed to settle for at least 3 hours and then the supernatant was drawn off via a cannula.

EXAMPLE 4

Two-Step Reduction of a Magnesium Halide with an Alkali Metal with a Catalytic Amount of Naphthalene Two 50 mL two-necked flasks, A and B, are equipped with rubber septa, condensers topped with argon inlets, and Teflon™-coated magnetic stir bars. Flask A is charged with freshly cut lithium (30.0 mmol) and a catalytic amount of naphthalene (1.5 mmol). Flask B is charged with $MgCl_2$ (15.0 mmol). Both of these operations are performed in an argon atmosphere drybox. The flasks are then transferred to a manifold system and fitted with argon inlets. Freshly distilled THF (15 mL) is added to both flask A and B via a syringe. The mixtures are stirred at room temperature. The magnesium chloride/THF solution is transferred dropwise to flask A by a cannula at a rate that allows the color of the solution to remain green.

EXAMPLE 5

Spiroannelation

Initial attempts to prepare a (2-butene-1,4-diyl)magnesium complex by reacting 1,2-dimethylenecyclo-hexane with ordinary metallic magnesium were not successful. Highly reactive magnesium, prepared by the reduction of magnesium chloride with lithium using naphthalene as an electron carrier, reacted smoothly with 1,2-dimethylenecyclohexane in THF at ambient temperature, giving the corresponding (2-butene-1,4-diyl)magnesium complex in high yield.

In a typical preparation, 1,2-dimethylenecyclo-hexane (2.0 mmol) was added via a disposable syringe to the newly prepared highly reactive Mg (3.0–4.0 mmol) in THF (15 mL). The mixture was stirred for 3–4 hours at room temperature under argon. The yellowish gold THF solution of the complex was separated from the excess magnesium either by: filtration; or by transferring the solution via cannula to another flask after the mixture had settled and the solution had became transparent (approximately 2 hours). Bis-electrophiles were added to the freshly prepared THF solutions of the magnesium complexes of 1,2-dimethylenecycloalkanes at –78° C. The reaction mixture was then stirred at –78° C. for 1 hour prior to warm up. This same method can be extended to other 1,2-dimethylene-cycloalkanes, such as 1,2-dimethylenecyclopentane and 1,2-dimethylenecycloheptane.

Significantly, treatment of this type of (2-butene-1,4-diyl)magnesium complex, i.e., those resulting from the reaction of highly reactive magnesium with cycloalkanes having two conjugated exocyclic double bonds, with bis-electrophiles, especially 1,n-dibromoalkanes, gave spirocycles in good to excellent yields. The results are summarized in Table I. A major advantage of using (2-butene-1,4-diyl)magnesium magnesium complexes is that spiroannelation can be achieved in one synthetic operation.

TABLE I

Reactions of the Magnesium Complexes of 1,2-Dimethylenecycloalkanes with Bis-electrophiles

| Diene[a] | Electrophile | Conditions | Product[b] | % Yield[c] |
|---|---|---|---|---|
| 1 | $Br(CH_2)_5Br$ | –78° C. to reflux | | 45 |
| 1 | $Br(CH_2)_4Br$ | –78° C. to reflux | | 75 (81) |
| 1 | $Br(CH_2)_3Br$ | –78° C. to room temp. | | 75 (87) |
| 1 | $Br(CH_2)_3Br$ | –78° C. to –30° C. | | 78[d] |

TABLE I-continued

Reactions of the Magnesium Complexes of 1,2-Dimethylenecycloalkanes with Bis-electrophiles

| Diene[a] | Electrophile | Conditions | Product[b] | % Yield[c] |
|---|---|---|---|---|
| 1 | Br(CH$_2$)$_2$Br | −78° C. to room temp. | | — (15)[e] |
| 1 | TsO(CH$_2$)$_2$OTs | −78° C. to room temp. | | 52 (67)[e] |
| 2 | Br(CH$_2$)$_3$Br | −78° C. to room temp. | | 60 (70) |
| 3 | Br(CH$_2$)$_3$Br | −78° C. to room temp. | | 77 (86) |

[a]1: 1,2-Dimethylenecyclohexane;
2: 1,2-Dimethylenecyclopentane;
3: 1,2-Dimethylenecycloheptane.
[b]All new compounds have been fully characterized by $^1$H NMR, $^{13}$C NMR, IR and mass spectra.
[c]Isolated overall yields were based on 1,2-dimethylenecycloalkanes. GC yields are shown in parentheses.
[d]Protonation of the intermediate at −30° C. resulted in monoalkylation, yielding the corresponding bromoolefin containing a quaternary center.
[e]Attempts to generate a four-membered ring by treating the (2-butene-1,4-diyl)magnesium complex generated from 1a with 1,2-dibromoethane gave only low yields of 5-methylenespiro[3.5]nonane. This spirocycle was prepared in good yield by the use ethylene glycol di-p-tosylate in place of 1,2-dibromoethane in THF at −78° C. followed by warming to room temperature.

EXAMPLE 6

Keto-Functionalized Carbocycles

The (2-butene-1,4-diyl)magnesium complexes prepared from the reaction of highly reactive magnesium with cycloalkanes having two conjugated exocyclic double bonds also react with bromoalkylnitriles to generate keto-functionalized carbocycles. These magnesium complexes of 1,2-dimethylenecycloalkanes were prepared as described above. The bromonitriles were added to the THF solution of these complexes at −78° C. The reaction mixture was then stirred at −78° C. for 30 minutes prior to warming to room temperature. This was followed by adding H$_3$$^+$ to the solutions. Table II summaries the results of these studies.

TABLE II

Reactions of the Magnesium Complexes of 1,2-Dimethylenecycloalkanes with Bromoalkylnitriles

| Diene[a] | Bromonitrile | Product[b] | % Yield[c] |
|---|---|---|---|
| 1 | BrCH$_2$CN | | 46 |

TABLE II-continued

Reactions of the Magnesium Complexes of
1,2-Dimethylenecycloalkanes with Bromoalkylnitriles

| Diene[a] | Bromonitrile | Product[b] | % Yield[c] |
|---|---|---|---|
| 1 | Br(CH$_2$)$_2$CN | 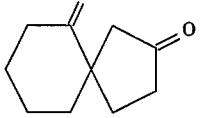 | 51 |
| | Br(CH$_2$)$_3$CN | 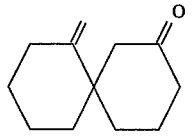 | 13 |
| 1 | Br(CH$_2$)$_3$CN | 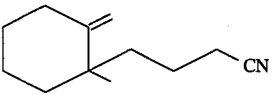 | 61[d] |
| 2 | Br(CH$_2$)$_2$CN | 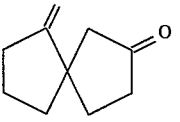 | 40 |
| 3 | Br(CH$_2$)$_2$CN | 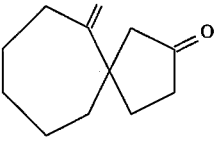 | 54 |

[a]1: 1,2-Dimethylenecyclohexane;
2: 1,2-Dimethylenecyclopentane;
3: 1,2-Dimethylenecycloheptane.
[b]All compounds have been completely characterized spectroscopically.
[c]Isolated overall yields were based on 1,2-dimethylenecycloalkanes.
[d]Protonation at −40° C. resulted in the survival of the cyano group, establishing where the initial attack occurred.

EXAMPLE 7

Fused Ring Carbocyclic Alcohols and β,δ-Unsaturated Ketones

Table III lists representative results for the reactions of magnesium complexes of 1,2-dimethylenecyclo-alkanes with carboxylic esters and acid halides. This approach is of general synthetic utility for the preparation of fused carbocyclic alcohols or β,δ-unsaturated ketones depending on the reaction temperatures. For example, treatment of the magnesium complex of 1,2-dimethylenecyclohexane with ethyl acetate at low temperatures (−78° C. to −10° C.) and protonating the reaction product with a mineral acid at −10° C. resulted in the formation of 2-methyl-1-cyclohexenyl-2-propanone in 72% isolated yield. On the other hand, warming the mixture to reflux followed by workup afforded a fused carbocyclic alcohol, in excellent yield.

The magnesium complexes of 1,2-dimethylenecycloalkanes were prepared as described above. The temperature of the reaction of each of these complexes with carboxylic esters or acid halides was typically maintained at or below −10° C. in order to obtain an enone product. In contrast, the reaction mixture was typically refluxed for complete formation of a fused carbocycle product. Satisfactory results were obtained in the reactions using ethyl acetate, ethyl butyrate, ethyl benzoate, and acetyl chloride.

TABLE III

Reactions of the Magnesium Complexes of 1,2-Dimethylenecycloalkanes with Esters and Acetyl Chloride

| Diene[a] | RC(O)X | Conditions[b] | Product[c] | % Yield[d] |
|---|---|---|---|---|
| 1 | CH$_3$COOEt | A | [bicyclic structure with OH, CH$_3$] | 91 |
| 1 | CH$_3$COOEt | B | [cyclohexene with CH$_2$C(O)CH$_3$] | 72 |
| 1 | CH$_3$COOEt then CH$_3$COCl | C | [methylenecyclohexane-cyclopropane with OCCH$_3$] | 75 |
| 1 | CH$_3$CH$_2$COOEt | A | [bicyclic structure with OH, propyl] | 96 |
| 1 | CH$_3$CH$_2$COOEt | B | [cyclopentene with CH$_2$C(O)propyl] | 81 |
| 1 | PhCOOEt | A | [bicyclic structure with OH, Ph] | 55 |
| 1 | PhCOOEt | B | [cyclohexene with CH$_2$C(O)Ph] | 62 |
| 2 | CH$_3$CH$_2$COOEt | A | [bicyclic structure with OH, propyl] | 59 |
| 2 | CH$_3$CHCOOEt | B | [cyclohexene with CH$_2$C(O)propyl] | 76 |
| 3 | CH$_3$CH$_2$COOEt | A | [bicyclic structure with OH, propyl] | 74 |
| 3 | CH$_3$CH$_2$COOEt | B | [cycloheptene with CH$_2$C(O)propyl] | 84 |
| 1 | CH$_3$COCl | A | [bicyclic structure with OH, CH$_3$] | 69 |
| 1 | CH$_3$COCl | D | [cyclohexene with CH$_2$C(O)CH$_3$] | 58 |

TABLE III-continued

Reactions of the Magnesium Complexes of 1,2-Dimethylenecycloalkanes with Esters and Acetyl Chloride

| Diene[a] | RC(O)X | Conditions[b] | Product[c] | % Yield[d] |
|---|---|---|---|---|
| 1 | 2CH₃COCl | E | (cyclohexane with methylene and cyclopropyl-OC(O)CH₃ substituent) | 88 |

[a]1: 1,2-Dimethylenecyclohexane;
2: 1,2-Dimethylenecyclopentane;
3: 1,2-Dimethylenecycloheptane.
[b]Conditions "A": stir at −78° C. for 30 minutes, allow solution to warm to room temperature, and then reflux for 30 minutes.
Conditions "B": stir at −78° C. for 30 minutes, allow solution to warm to −10° C., and then stir at −10° C. for 1 hour.
Conditions "C": stir at −78° C. for 30 minutes, allow solution to warm to −10° C., and then stir at −10° C. for 1 hour, add CH₃COCl at −20° C. and stir for 30 minutes, warm to room temperature.
Conditions "D": stir at −78° C. for 30 minutes, allow solution to warm to −20° C., and then stir at −20° C. for 30 minutes.
Conditions "E": stir at −78° C. for 30 minutes, allow solution to warm to room temperature.
[c]All new compounds have been fully characterized by $^1$H NMR, $^{13}$C NMR, IR and mass spectra.
[d]Isolated overall yields were based on 1,2-dimethylenecycloalkanes.

EXAMPLE 8

γ-Lactones Including Spiro γ-Lactones

The (2-butene-1,4-diyl)magnesium complexes prepared from the reaction of highly reactive magnesium with either cyclic hydrocarbons having at least two conjugated exocyclic double bonds or open-chain conjugated dienes also react with a ketone or aldehyde and carbon dioxide to form γ-lactones, preferably spiro γ-lactones. Magnesium complexes of 1,2-dimethylenecycloalkanes and 1,3-butadienes were prepared as described above. A molar equivalent of a ketone was added to the THF solution of these complexes at −78° C. The reaction mixture was then stiffed for ten minutes, warmed to a temperature of 0° C. to 25° C., and bubbled with carbon dioxide for twenty minutes prior to protonation and warming to about 40° C. Table IV summarizes the results of these studies.

In a typical reaction 1,2-dimethylenecyclohexane (0.239 g, 2.21 mmol) was added via a disposable syringe to the highly reactive magnesium (3.53 mmol) in THF (20 mL). After being stiffed at room temperature for 4 hours, the reaction mixture was allowed to stand until the solution became transparent (approximately 2 hours). The yellowish gold THF solution of the complex was then separated from the excess magnesium by cannulating the solution to another flask under argon. The THF solution of newly formed magnesium complex of 1,2-dimethylenecyclohexane was cooled to −78° C. using a dry ice/acetone bath, and acetone (0.122 g, 2.10 mmol) was added via a disposable syringe. The mixture was stirred at −78° C. for 10 minutes, then gradually warmed to 0° C. Carbon dioxide was then bubbled through the reaction mixture for 10 minutes at 0° C., and another 10 minutes at room temperature. An aqueous solution of 1.5 N HCl (10 mL) was added at 0° C. The reaction mixture was slightly heated at 40° C. for 1 hour. After cooling to room temperature, the mixture was extracted with diethyl ether (3×20 mL). The combined organic phases were washed with saturated aqueous NaHCO₃ (2×20 mL) and brine (20 mL) and dried over anhydrous MgSO₄. Removal of solvents and flash column chromatography gave 4,4-dimethyl-6-methylene-3-oxaspiro[4.5]decan-2-one (0.279 g) in 68% yield. The following scheme illustrates this route for spiro γ-lactone synthesis.

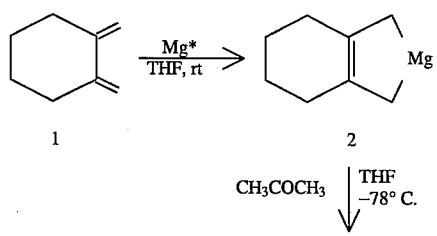

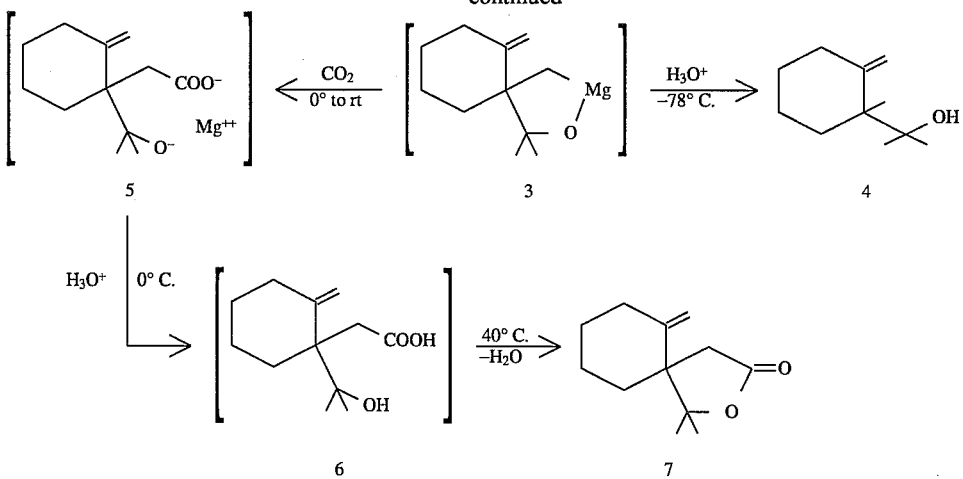

Referring to the above scheme, initially it was observed that treatment of 1,2-dimethylenecyclohexane-magnesium (2) with one molar equivalent of acetone at −78° C. resulted in the formation of a 1,2-addition adduct (3) derived from the incorporation of one molecule of acetone with the diene complex. (The actual structure of this complex is unknown.) Protonation of the adduct (3) at −78° C. yielded a tertiary alcohol containing a quaternary center (4). Carbon dioxide was bubbled as a second electrophile through the reaction mixture at 0° C. to room temperature. Intermediate (3) reacted quickly with carbon dioxide, yielding presumably a magnesium salt of an organic molecule containing both an alkoxy and a carboxylate group (5). After protonation followed by slight warming, a spiro γ-lactone, 4,4-dimethyl-6-methylene-3-oxaspir[4.5]decan-2-one (7) was obtained. Treatment of (2) with two molar equivalents of acetone at −78° C. followed by acidic hydrolysis at −78° C. also yielded (4), indicating that the initially formed adduct (3) did not undergo further addition with unreacted acetone under the reaction conditions. Thus, both acetone and subsequently added $CO_2$ were delivered to the original diene at desired positions.

Significantly, this approach can also be used to prepare spiro γ-lactones containing two spiro centers. The representative examples of this dispiroannelation are listed in Table IV (Entries 2 and 3). For example, (2) was treated with cyclopentanone at −78° C. and the reaction mixture was then bubbled with $CO_2$ at 0° C. to room temperature. Workup gave 11-methylene-14-oxadispiro[4.0.5.3]tetradecan-13-one in 66% isolated yield (Table IV, Entry 2). Similar chemistry was observed when cyclohexanone was used as the first electrophile (Table IV, Entry 3).

A notable advantage of this new γ-lactone synthesis is that the construction of a quaternary center and the introduction of both a hydroxyl and a carboxyl used for lactonization are accomplished in one synthetic operation. Remarkably, this chemistry has been easily extended to the magnesium complex of acyclic 1,3-diene. The following scheme gives an outline for the synthesis of spiro γ-lactones from (2,3-dimethyl-2-butene-1,4-diyl)magnesium (11). Generally, reaction of a cyclic ketone with (11) at −78° C. resulted in initial attach at the 2-position of the diene complex, giving an internal alkoxy Grignard (12). After warming up, the intermediate was allowed to react with carbon dioxide at 0° C. to room temperature. Upon protonation and gentle heating, a spiro γ-lactone containing a quaternary center was obtained (14) (Table IV, Entries 4 and 5). The method is equally useful for the preparation of γ-lactones. Use of an acyclic ketone or aldehyde instead of a cyclic ketone will result in the synthesis of the corresponding γ-lactone.

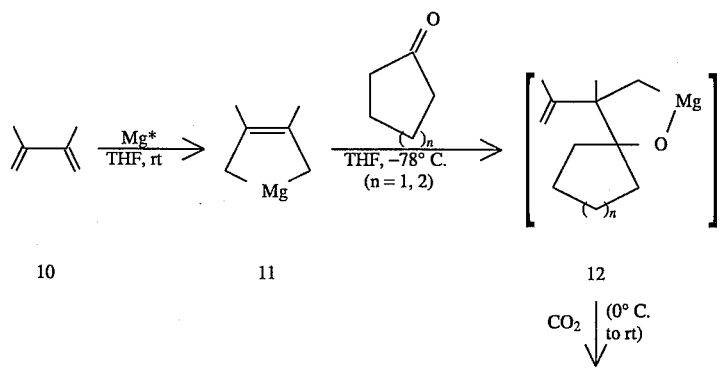

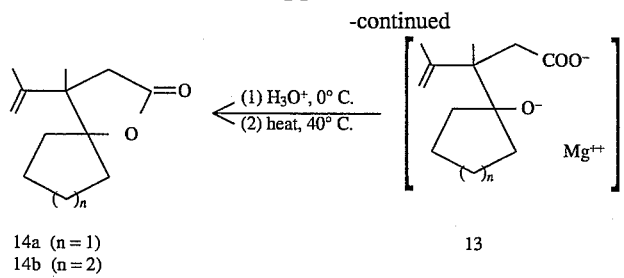

14a (n = 1)
14b (n = 2)

TABLE IV

Synthesis of Spiro γ-Lactones from Conjugated Diene, Ketone and $CO_2$

| Entry | Diene[a] | Ketone[b] | Product[c] | % Yield[d] |
|---|---|---|---|---|
| 1 | 1 | Acetone | | 68 |
| 2 | 1 | Cyclopentanone | | 66 |
| 3 | 1 | Cyclohexanone | | 60 |
| 4 | 4 | Cyclopentanone | | 68 |
| 5 | 4 | Cyclohexanone | | 61 |

[a]1: 1,2-Dimethylenecyclohexane;
4: 2,3-Dimethyl-1,3-butadiene.
[b]Ketone was added to the diene-magnesium complex at −78° C. and the mixture was stirred at −78° C. for 10 minutes, then gradually warmed to 0° C. followed by the bubbling of $CO_2$.
[c]All products have been fully characterized spectroscopically, including $^1H$ NMR, $^{13}C$ NMR, FTIR, MS and high resolution mass spectra.
[d]Isolated yields.

EXAMPLE 9

Spiroheterocycles

Spiroheterocyclic compounds, particularly silicon-containing spiroheterocyclic compounds, can be prepared from the reaction of unsymmetrical (2-butene-1,4-diyl)magnesium complexes with a tetrahalide reagent of the formula $MX_4$ (wherein M=Si, Ge, Sn, Pb and X=F, Cl, Br, I). Preferably, a silicon tetrahalide is used for the preparation of silicon-containing spiroheterocycles. The results for silicon-containing spiroheterocycles are summarized in Table V.

In a typical reaction, (2-methyl-2-butene-1,4-diyl)magnesium in 20 mL of THF, which was freshly prepared from isoprene (0.250 g, 3.67 mmol) and excess highly reactive magnesium, was cooled to −78° C. $SiCl_4$ (0.256 g, 1.50 mmol) was added via a disposable syringe. There was an instantaneous disappearance of a pale orange color. After being stirred at −78° C. for 1 hour, the mixture was gradually warmed to 0° C. and an aqueous solution of 1.5N HCl (15 mL) was added. The reaction mixture was washed with diethyl ether (20 mL). The aqueous layer was extracted with diethyl ether (2×20 mL). The organic portions were combined, washed with saturated aqueous $NaHCO_3$ (2×20 mL) and brine (15 mL), and dried over anhydrous $Na_2SO_4$. Evaporation of solvents and flash column chromatography afforded 2,7-dimethyl-5-silaspiro[4,4]nona-2,7-diene. This compound has been previously reported to be difficult to prepare; however, utilization of magnesium complexes of 1,3-dienes allows the preparation to be carded out under extremely mild conditions.

TABLE V

Preparation of Silicon-Containing Spiroheterocycles from Substituted (2-butene-1,4-diyl)Magnesium

| Diene[a] | Electrophile[b] | Product(s)[c] | % Yield |
|---|---|---|---|
| 4 | SiCl$_4$ |  | 75 |
| 5 | SiCl$_4$ | 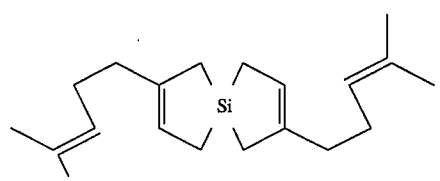 | 62 |
| 6 | SiCl$_4$ | 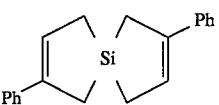 | 34 |

[a]4: isoprene;
5: myrcene;
6: 2-phenyl-1,3-butadiene.
[b]Electrophiles were added to the THF solution of substituted (2-butene-1,4-diyl)magnesium complexes at −78° C. The reaction mixture was stirred at −78° C. for 30 minutes then warmed to 0° C. prior to workup.
[c]All new compounds were completely characterized spectroscopically.

2,7-Dimethyl-5-silaspiro[4,4]nona-2,7-diene (0.185 g, 75 yield): $^1$H NMR δ5.53 (m, 2H), 1.77 (t, J=1.0 Hz, 6H), 1.48 (d, J=1.1 Hz, 4H), 1.40 (s, 4H); $^{13}$C NMR δ140.2, 124.9, 22.6, 21.8, 17.8; IR (neat) 3005, 2958, 2927, 2908, 2879, 2848, 1637, 1448, 1433, 1213, 1161, 1022, 756 cm$^{-1}$; EIMS m/z (relative intensity) 164 (M$^+$, 73), 149 (3), 136 (8), 122 (12), 109 (4), 96 (100).

2,7-Di(4-methyl-3-pentenyl)-5-silaspiro[4,4]nona-2,7-diene (62% yield): $^1$H NMR δ5.55 (s, 2H), 5.09 (s, 2H), 2.09 (s, 8H), 1.67 (s, 6H), 1.59 (s, 6H), 1.47 (s, 4H), 1.40 (s, 4H); $^{13}$C NMR δ144.2, 131.3, 124.5, 124.1, 36.8, 26.4, 25.7, 19.4, 17.7, 17.3; IR (neat) 3001, 2966, 2912, 2879, 1631, 1448, 1375, 1161, 823, 760; EIMS m/z (relative intensity) 300 (M$^+$, 15), 257 (6), 231 (9), 203 (4), 175 (5), 163 (100), 135 (6), 121 (3), 109 (7), 95 (13), 69 (44); HRMS calcd for C$_{20}$H$_{32}$Si: 300.2273, found: 300.2278. Anal. calcd: C, 79.93; H, 10.73. Found: C, 80.24; H, 11.12.

2,7-Diphenyl-5-silaspiro[4,4]nona-2,7-diene (34% yield): $^1$H NMR δ7.5–7.49 (m, 4), 7.36–7.20 (m, 6H), 6.44 (s, 2H), 1.96 (s, 4H), 1.80 (s, 4H); $^{13}$C NMR δ141.9, 140.4, 128.2, 127.1, 126.8, 125.6, 18.3, 18.2; IR (neat) 3080, 3057, 3020, 2916, 2879, 1604, 1493, 1444, 1159, 997, 767, 742, 694 cm$^{-1}$; EIMS m/z (relative intensity) 288 (M$^+$, 100), 158 (57), 105 (15), 71 (14); HRMS calcd for C$_{20}$H$_{20}$Si: 288.1334, found: 288.1328.

EXAMPLE 10

Regioselective Reactions

Unsymmetrical (2-butene-1,4-diyl)magnesium complexes were prepared as follows. Isoprene, myrcene, or 2-phenyl-1,3-butadiene was added to an excess of newly generated highly reactive magnesium in 20 mL of THF (typical ratio of Mg:diene=1.5:1 to 1.8:1). After being stirred at room temperature for 2 hours, the reaction mixture was allowed to stand until the solution became transparent (approximately 3 hours). Then the upper clear solution of magnesium complex was transferred via a cannula to another flask under argon. The appropriate electrophile was then added to this magnesium complex.

In a typical regioselective reaction of an unsymmetrical (2-butene-1,4-diyl)magnesium complex, a THF solution of the complex (20 mL) prepared from isoprene (0.281 g, 2.06 mmol, technical grade) and activated magnesium (3.44 mmol) was cooled to −78° C. Me$_3$SiCl (0.171 g, 1.57 mmol) was added via a disposable syringe. The reaction mixture was stirred at −78° C. for 1 hour, and then it was gradually warmed to 0° C. Excess cyclohexanone (0.278 g, 2.83 mmol) was added at 0° C. The reaction mixture was warmed to room temperature and stirred for 1 hour. An aqueous solution of HCl (1.5N, 10 mL) was added at 0° C. The mixture was washed with diethyl ether (20 mL), and the aqueous layer was extracted with diethyl ether (2×20 mL). The combined organic phases were washed with a saturated aqueous solution of NaHCO$_3$ (2×15 mL) and brine (20 mL) and dried over MgSO$_4$. Removal of solvents and flash column chromatography (eluted by hexanes/Et$_2$O, 98:2) gave 1-(2-methyl-1-trimethylsilymethyl-2-propenyl)cyclohexanol as the major isomer (0.372 g, 77%) and 1-(1-methyl-1-trimethylsilylmethyl-2-propenyl)cyclohexanol as the minor isomer (0.025 g, 5%) the major isomer was eluted out before the minor isomer in 82% total yield.

TABLE VI

Regioselective Reactions of Unsymmetrical (2-butene-1,4-diyl)magnesium Complexes with Two Different Electrophiles

| Diene[a] | R₃SiCl[b] | Product(s)[c,d] | % Yield |
|---|---|---|---|
| 4 | (CH₃)₃SiCl | (77:23) | 91 |
| 4 | (n-Butyl)₃SiCl | (92:8) | 94 |
| 5 | (CH₃)₃SiCl | (94:6) | 82 |
| 5 | (n-Butyl)₃SiCl | | 94 |
| 6 | (CH₃)₃SiCl | | 95 |
| 6 | (n-Butyl)₃SiCl | | 92 |

[a] 4: isoprene;
5: myrcene;
6: 2-phenyl-1,3-butadiene.
[b] R₃SiCl was added at −78° C. The reaction mixture was stirred at −78° C. for 1 hour and then warmed to 0° C. prior to the addition of cyclohexanone.
[c] The compositions of all products (or major isomers) were determined by high resolution mass spectroscopy and/or elemental analyses. The structures of all compounds were established by ¹H NMR, ¹³C NMR, IR and mass spectra.
[d] Ratios of isomers were given in parentheses. Individual isomers were separated by chromatography.

1-(2-Methyl-1-trimethylsilylmethyl-2-propenyl)cyclohexanol or 1-(1-Methyl-1-trimethylsilymethyl-2-propenyl)cyclohexanol (77:23, 91% total yield). Major isomer: $^1$H NMR δ4.85 (m, 1H), 4.76 (m, 1H), 2.14 (dd, J=11.7, 3.4 Hz, 1H), 1.74 (dd, J=1.2, 0.7 Hz, 3H), 1.65–1.10 (m, 10H), 0.8–0.68 (m, 2H), −0.03 (s, 9H); $^{13}$C NMR 147.0, 114.1, 73.0, 52.6, 35.6, 35.5, 25.8, 22.3, 22.1, 14.0, −1.1; IR (neat) 3487 (br), 3068, 2933, 2858, 1639, 1448, 1373, 1246, 964, 889, 862, 841 cm$^{-1}$; HRMS (FAB) calcd for $[C_{14}H_{28}OSi+Li]+$: 247.2070, found: 247.2075. Anal. Calcd for $C_{14}H_{28}OSi$: C, 69.93; H, 11.74. Found: C, 69.46; H, 11.97. Minor isomer: $^1$H NMR δ5.91 (dd, J=17.6, 10.8 Hz, 1H), 5.13 (dd, J=10.8, 1.6 Hz, 1H), 5.01 (dd, J=17.6, 1.6 Hz, 1H), 1.67–1.20 (m, 10H), 1.08 (d, J=1.0 Hz, 3H), 0.95 (dd, J=14.2, 1.0 Hz, 1H), 0.80 (d, J=14.2 Hz, 1H), −0.01 (s, 9H); $^{13}$C NMR δ145.6, 114.0, 75.3, 46.8, 31.3, 30.5, 25.8, 24.2, 22.2, 22.0, 19.4, 1.00; IR (neat) 3492 (br), 3080, 2935, 2860, 1631, 1448, 1415, 1375, 1248, 1223, 910, 864, 839 cm$^{-1}$; EIMS m/z (relative intensity) 225 ($[M-CH_3]^+$, 0.7), 207 (0.6), 183 (0.3), 171 (5.3), 142 (12), 99 (27), 73 (100); HRMS calcd for $C_{14}H_{28}OSi$ and $[M-CH_3]$: 240.1909, 225.1675, found: 240.1897 (EI Peak Match), 225.1678.

1-(2-Methyl-1-tri(n-butyl)silylmethyl-2-propenyl)cyclohexanol and 1-(1-Methyl-1-(tri-n-butyl)silylmethyl-2-propenyl)cyclohexanol (92:8, 94% total yield). Major isomer: $^1$H NMR δ4.85 (m, 1H), 4.77 (d, J=1.9 Hz, 1H), 2.12 (dd, J=8.5, 6.1 Hz, Hz, 1H), 1.76 (d, J=0.4 Hz, 3H), 1.68–1.10 (m, 22H), 0.87 (t, J=7.0 Hz, 9H), 0.76–0.70 (m, 2H), 0.5–4.44 (m, 6H); $^{13}$C NMR δ147.2, 114.1, 73.2, 52.3, 35.6, 35.5, 26.9, 26.2, 25.9, 22.3, 22.2, 13.8, 12.4, 9.8; IR (neat) 3491 (br), 3068, 2954, 2924, 2870, 2856, 1637, 1456, 1375, 1196, 1082, 964, 887 cm$^{-1}$; EIMS m/z (relative intensity) 309 ($[M-C_4H_9]^+$, 0.5), 297 (4.3), 268 (7.8), 199 (100), 143 (67), 99 (19); HRMS calcd for $C_{23}H_{46}OSi$ and $C_{22}^{13}CH_{46}OSi$: 366.3318, 367.3347, found (EI Peak Match): 366.3301, 367.3338. Anal. Calcd: C, 75.33; H, 12.64. Found: C, 75.60; H, 12.77. Minor Isomer (difficult to isolate): $^1$H NMR δ5.92 (dd, J=17.6, 10.8 Hz, 1H), 5.11 (dd, J=10.8, 1.2 Hz, 1H), 5.01 (dd, J=17.6, 1.2 Hz, 1H), 1.70–1.10 (m, 22H), 1.07 (s, 3H), 0.88 (t, J=7.0 Hz, 9H), 0.9–0.75 (m, 2H), 0.5–0.45 (m, 6H).

1-(2-(4-Methyl-3-pentenyl)-1-trimethylsilylmethyl-2-propenyl)eyclohexanol and 1-(1-Ethenyl-5-methyl-1-trimethylsilylmethyl-4-hexenyl)cyclohexanol (94:6). Major isomer: $^1$H NMR δ5.17–5.09 (m, 1H), 4.89 (s, 1H), 4.86 (s, 1H), 2.20–2.00 (m, 5H), 1.67 (s, 3H), 1.60 (s, 3H), 1.68–1.05 (m, 10H), 0.84–0.69 (m, 2H), 0.03 (s, 9 H); $^{13}$C NMR δ151.1, 131.5, 124.4, 111.4, 73.2, 53.0, 35.6, 35.5, 25.9, 25.8, 25.7, 22.3, 22.1, 17.6, 14.9, −0.9; IR (neat) 3485 (br), 3080, 2931, 2858, 1633, 1448, 1375, 1246, 972, 891,860, 837 cm$^{-1}$; EIMS m/z (relative intensity) 290 ($[M-H_2O]^+$, 0.3), 275 (0.2), 210 (7), 171 (28), 141 (87), 99 (16), 73 (100); HRMS calcd for $C_{19}H_{36}OSi$ and $C_{18}^{13}CH_{36}OSi$: 308.2535, 309.2563, found (HREI Peak Match): 308.2530, 309.2559. Anal. Calcd: C, 73.96; H, 11.76. Found: C, 74.15; H, 11.80. Minor isomer: $^1$H NMR δ5.81 (dd, J=17.6, 11.0 Hz, 1H), 5.1–4.95 (m, 3H), 2.10–0.95 (m, 14H), 1.65 (s, 3H), 1.59 (s, 3H), 0.91 (d, J=15.0 Hz, 1H), 0.75 (d, J=15.0 Hz, 1H), 0.04 (s, 9H); $^{13}$C NMR δ145.5, 131.0, 125.3, 114.1, 75.8, 50.6, 33.3, 31.6, 31.5, 25.7, 24.0, 22.0, 21.8, 19.8, 17.8, 1.6; IR (neat) 3566 (br), 3080, 2933, 2858, 1631, 1450, 1375, 1259, 1246, 1155, 958, 912, 860, 845 cm$^{-1}$.

1-(2-(4-Methyl-3-pentenyl)-1-tri(n-butyl)silylmethyl-2-propenyl)cyclohexanol (94 % yield): $^1$H NMR δ5.17–5.09 (m, 1H), 4.89 (s, 1H), 4.88 (s, 1H), 2.20–2.03 (m, 5H), 1.67 (s, 3H), 1.60 (s, 3H), 1.70–1.10 (m, 22H), 0.86 (t, J=7.2 Hz, 9H), 0.78–0.73 (m, 2H), 0.50–0.43 (m, 6H); $^{13}$C NMR δ151.2, 131.5, 124.3, 111.0, 73.4, 52.6, 35.6, 35.3, 26.9, 26.1, 25.9, 25.8, 25.7, 22.3, 22.1, 17.6, 13.8, 12.5, 10.5; IR (neat) 3491 (br), 3080, 2954, 2922, 2870, 2856, 1633, 1456, 1375, 1194, 964, 887 cm$^{-1}$; EIMS m/z (relative intensity) 336 ($[M-C_6H_{10}O]^+$, 2.3), 297 (1.9), 199 (100), 159 (39), 143 (53), 103 (18); HRMS calcd for $C_{28}H_{54}OSi$ and $C_{27}^{13}CH_{54}OSi$: 434.3944, 435.3973, found (EI Peak Match): 434.3932, 435.3961. Anal. Calcd: C, 77.34;H, 12.53. Found: C, 77.22; H, 12.42.

1-(2-Phenyl-1-trimethylsilylmethyl-2-propenyl)cyclohexanoi (95% yield): $^1$H NMR 7.43 (m, 2H), 7.30 (m, 2H), 7.23 (m, 1H), 5.50 (s, 1H), 5.16 (s, 1H), 2.83 (t, J=6.9 Hz, 1H), 1.69–1.00 (m, 10H), 0.97 (d, J=6.9 Hz, 2H), −0.03 (s, 9H); $^{13}$C NMR δ150.5, 144.5, 128.3, 127.1, 126.6, 115.5, 74.1, 48.7, 35.6, 35.0, 25.7, 22.0, 21.9, 16.9, −0.5; IR (neat) 3483 (br), 3082, 3057, 3030, 2935, 2860, 1618, 99, 1574, 1495, 1448, 1248, 966, 903, 862, 843, 704 cm$^{-1}$; EIMS m/z (relative intensity) 284 ($[M-H_2O]^+$, 0.3), 272 (0.3), 204 (30), 130 (8), 99 (13), 73(100); HRMS (FAB) calcd for $[C_{19}H_{30}OSi+Li]$: 309.2226, found 309.2221.

1-(2-Pheny-1-tri(n-butyl)silylmethyl-2-propenyl)cyclohexanol (92% yield): $^1$H NMR δ7.50–7.45 (m, 2H), 7.3–7.28 (m, 2H), 7.27–7.21 (m, 1H), 5.53 (s, 1H), 5.20 (s, 1H), 2.83 (dd, J=11.3, 3.5 Hz, 1H), 1.7–0.89 (m, 24H), 0.85 (t, J=7.0 Hz, 9H), 0.5–0.43 (m, 6H); $^{13}$C NMR δ150.4, 144.2, 128.3, 127.1, 126.6, 115.0, 74.4, 48.6, 35.6, 34.9, 26.8, 26.1, 25.8, 22.0, 13.7, 12.7; IR (neat) 3487 (br), 3082, 3055, 3028, 2952, 2922, 2870, 2856, 1616, 1599, 1574, 1495, 1464, 1375, 1080, 964, 903, 706 cm$^{-1}$; EIMS m/z (relative intensity) 330 ($[M-C_6H_{10}O]^+$, 2.2), 273 (1.2), 199 (38), 143 (68), 101 (18), 69 (100); HRMS calcd for $C_{28}H_{48}OSi$ and $C_{27}^{13}CH_{48}OSi$: 428.3474, 429.3504, found (EI Peak Match): 428.3467, 429.3507.

EXAMPLE 11

Preparation of δ-Lactones

In a typical procedure, 1,2-bis(methylene)cyclohexane (0.330 g, 3.05 mmol) was added via a disposable syringe to the highly reactive magnesium (4.68 mmol) in freshly distilled THF (15 ml). After being stirred at ambient temperature for several hours, the reaction mixture was allowed to stand until it became transparent (approximately 2 hours). The yellowish-gold THF solution of the complex was then separated from the excess magnesium by cannulating the solution to another flask under argon. The THF solution of the newly formed magnesium complex of 1,2-dimethylenecyclohexane was cooled to −78° C. using a dry ice/acetone bath. Ethylene oxide (1 ml) was condensed into a small vial, capped with a rubber septum (at −78° C.) and was subsequently added to the reaction mixture via cannula. The mixture was stirred for 30 minutes at −78° C., then gradually warmed to 0° C. At this point, the reaction mixture was bubbled with purified carbon dioxide for 10 minutes at 0° C. and another 10 minutes at room temperature. An aqueous solution of 3N HCl (10 ml) was added via syringe at 0° C. The reaction mixture was then slightly heated to 40° C. After subsequent cooling to ambient temperature, the mixture was extracted with diethyl ether (3×20 ml). The combined organic phases were washed with saturated aqueous NaHCO$_3$ (2×20 ml), water (1×20 ml), and dried over anhydrous MgSO$_4$. The solvents were then removed under vacuum and the remainder sample flash chromatographed to afford the δ-lactone, 7-methylene-3-oxaspiro[5.5]undecan-2-one (0.378 gm) in 69% yield. See Table VII for examples of compounds that can be prepared using this method. If carbon dioxide is not used, and the epoxide/diene-magnesium addition adducts are hydrolyzed with acid, alcohols are produced. See Table VIII for examples of compounds that can be prepared using this method.

TABLE VII

Reactions of Conjugated Diene-Magnesium Complexes with Epoxides Followed by Carbon Dioxide

| Entry | Diene | Epoxide | Product |
|---|---|---|---|
| 1 | | | |
| 2 | | | |
| 3 | | | |
| 4 | | | |
| 5 | | | |

TABLE VIII

Reactions of Conjugated Diene-Magnesium Complexes with Epoxides Followed by Acidic Hydrolysis

| Entry | Diene | Epoxide | Product |
|---|---|---|---|
| 1 | | | |
| 2 | | | |

TABLE VIII-continued

Reactions of Conjugated Diene-Magnesium Complexes
with Epoxides Followed by Acidic Hydrolysis

| Entry | Diene | Epoxide | Product |
|---|---|---|---|
| 3 | (2,3-dimethyl-1,3-butadiene) | 1,2-epoxybutane | 3,4-dimethyl-hex-3-en-... |
| 4 | (2,3-dimethyl-1,3-butadiene) | 1,2-epoxyhexane | corresponding homoallylic alcohol |
| 5 | (2,3-dimethyl-1,3-butadiene) | (R)-2-methyl-glycidol | chiral diol |
| 6 | 1,2-bis(methylene)cyclohexane | (R)-2-methyl-glycidol | chiral diol |

EXAMPLE 12

Preparation of γ-Lactams

In a typical reaction, 2,3-dimethyl-1,3-butadiene (1.5 ml) was added via disposable syringe to the active magnesium (4.64 mmol) in freshly distilled THF (15 ml). After being stirred at room temperature for 8 hours, the reaction mixture was allowed to stand until the solution became transparent (approximately 2 hours). The pale orange solution of the magnesium complex was then separated from the excess magnesium by cannulating the solution to another flask. The THF solution of the newly formed magnesium-diene complex was then cooled to −78° C. using a dry ice/acetone bath. N-benzylidieneaniline (0.547 gm, 3.02 mmol) was weighed into a small vial, capped with a rubber septum, evacuated, and charged with argon. Freshly distilled THF (5 mL) was then added to the vial. This was then added via cannule to the magnesium-diene solution at −78° C. Subsequent to being stirred for 30 minutes, the reaction mixture was then allowed to warm gradually to 0° C. Carbon dioxide was then bubbled through the reaction mixture for 10 minutes at 0° C. and another 10 minutes at room temperature. An aqueous solution of 3N HCl (10 ml) was added to the reaction mixture via syringe at 0° C. The reaction mixture was slightly heated at 40° C. for 1 hour. After cooling to room temperature, the mixture was extracted with diethyl ether (3×20 ml). The combined organic phases were washed with saturated aqueous NaHCO$_3$ (2×20 ml), water (1×20 ml), and then dried over anhydrous MgSO$_4$. After removal of solvents under vacuum, the residue is flash chromatographed on silica gel using gradient mixtures of hexanes and ethyl acetate to give N-benzyl-γ-lactam in 47% yield.

EXAMPLE 13

Preparation of Chiral Vicinal Diols

In a typical reaction, 1,2-bis(methylene)cyclohexane (0.303 gm, 2.80 mmol) was added via disposable syringe to the highly reactive magnesium (4.64 mmol) in freshly distilled THF (15 ml). After being stirred at ambient temperature for 4 hours, the reaction mixture was allowed to stand until the solution became transparent (approximately 2 hours). The yellow THF solution of the magnesium complex was then separated from the excess magnesium by cannulating the solution to another flask. The THF solution of newly formed magnesium complex of 1,2-dimethylenecyclohexane was cooled to −78° C. using a dry ice/acetone bath, and (R)-2-methyl-glycidol (0.109 gm, 1.23mmol) was added via disposable syringe. The mixture was stirred at −78° C. for 30 minutes and gradually warmed to 0° C. Ammonium chloride (5 ml) was added to the reaction mixture via disposable syringe. After warming to ambient temperature, the mixture was extracted with diethyl ether (3×20 ml) and the combined organic layers were dried over anhydrous MgSO$_4$. Removal of the solvents and flash column chromatography gave a vicinal diol in 62% yield.

The foregoing detailed description has been given for clarity of understanding only and no unnecessary limitations are to be understood therefrom. The invention is not limited to the exact details shown and described, for obvious modifications will occur to those skilled the art.

What is claimed is:

1. A method for the preparation of carbocycles comprising:

(a) contacting a magnesium(II) salt in an ethereal, polyethereal, or hydrocarbon solvent with a reducing agent having a reduction potential of about −1.5 volts, or more negative, relative to SCE, to form a highly reactive magnesium species;

(b) contacting the highly reactive magnesium species with a cyclic hydrocarbon containing at least two conjugated exocyclic double bonds to form a (2-butene-1,4-dyl)magnesium complex; and (c) contacting the (2-butene-1,4-diyl)magnesium complex with an electrophile to form a carbocycle.

2. The method of claim 1 wherein the step of contacting the (2-butene-1,4-diyl)magnesium complex with an electrophile comprises:

(a) contacting the (2-butene-1,4-diyl)magnesium complex with a carboxylic ester or acid halide in an ethereal or polyethereal solvent at a temperature of about −78° C. to −10° C. to from an intermediate; and (b) heating the intermediate to a temperature of about 25° C. or greater to form a fused ring carbocyclic alcohol.

3. The method of claim 1 wherein the step of contacting the (2-butene-1,4-diyl)magnesium complex with an electrophile comprises:
   (a) contacting the (2-butene-1,4-diyl)magnesium complex with a carboxylic ester or acid halide in an ethereal or polyethereal solvent at a temperature of about −78° C. to about −10° C. to form an intermediate; and
   (b) protonating this intermediate at a temperature no greater than about 0° C. to form a carbocycle containing a β,δ-unsaturated ketone functionality.

4. The method of claim 1 wherein the step of contacting the (2-butene-1,4-diyl)magnesium complex with an electrophile comprises:
   (a) contacting the (2-butene-1,4-diyl)magnesium complex with a carboxylic ester or first acid halide in an ethereal or polyethereal solvent at a temperature of below about −10° C; and
   (b) adding a second acid halide to form a carbocyclic spirocycle containing a three-membered ring.

5. A method for the preparation of a spiroheterocycle comprising:
   (a) contacting a magnesium(II) salt in an ethereal, polyethereal, or hydrocarbon solvent with a reducing agent having a reduction potential of about −1.5 volts, or more negative, relative to SCE, to form a highly reactive magnesium species;
   (b) contacting the highly reactive magnesium species with a 1,3-diene to form a (2-butene-1,4-diyl)magnesium complex; and
   (c) contacting the (2-butene-1,4-diyl)magnesium complex with a tetrahalide reagent of the formula $MX_4$, wherein M=Ge, Sn, Pb and X=F, Cl, Br, I, to form a spiroheterocycle.

6. The method of claim 5 wherein the highly reactive magnesium species is contacted with a symmetrical 1,3-diene.

7. The method of claim 5 wherein the highly reactive magnesium species is contacted with an unsymmetrical 1,3-diene.

8. The method of claim 7 wherein the unsymmetrical 1,3-diene is selected from the group consisting of isoprene, myrcene, and 2-phenyl-1,3-butadiene, to form an unsymmetrical (2-butene-1,4-diyl)magnesium complex.

9. The method of claim 5 wherein the tetrahalide reagent is $SiCl_4$.

10. A method for the control of the regioselectivity of electrophilic attack of unsymmetrical (2-butene-1,4-diyl)magnesium complexes comprising reacting the unsymmetrical (2-butene-1,4-diyl)magnesium complex with a triorganosilyl chloride prior to adding a second electrophile.

11. A method for the preparation of δ-lactones comprising:
   (a) contacting a magnesium(II) salt in an ethereal, polyethereal, or hydrocarbon solvent with reducing agent having a reduction potential of about −1.5 volts, or more negative, relative to SCE, to form a highly reactive magnesium species;
   (b) contacting the highly reactive magnesium species with a conjugated diene, to form a (2-butene-1,4-diyl)magnesium complex;
   (c) contacting the (2-butene-1,4-diyl)magnesium complex with an epoxide to form a 1,2-addition adduct of the (2-butene-1,4-diyl)magnesium complex and epoxide;
   (d) contacting the 1,2-addition adduct with $CO_2$ to form a nucleophilic addition product; and
   (e) contacting the nucleophilic addition product with an aqueous acid to form a δ-lactone.

12. The method of claim 11, wherein the conjugated diene is a cyclic hydrocarbon containing at least two conjugated exocyclic double bonds.

13. The method of claim 11, wherein the conjugated diene is an open chain conjugated diene.

14. The method of claim 11, wherein the step of contacting the (2-butene-1,4diyl)magnesium complex with an epoxide is carried out at a temperature of about −90° C. to about −70° C.

15. The method of claim 11, wherein the step of contacting the nucleophilic addition product with an aqueous acid includes the step of warming the reaction mixture to a temperature of about 30° C. to about 50° C.

16. The method of claim 11, wherein the epoxide is an unsymmetric epoxide.

17. A method for the preparation of γ-lactams comprising:
   (a) contacting a magnesium(II) salt in an ethereal, polyethereal, or hydrocarbon solvent with reducing agent having a reduction potential of about −1.5 volts, or more negative, relative to SCE, to form a highly reactive magnesium species;
   (b) contacting the highly reactive magnesium species with a conjugated diene, to form a (2-butene-1,4-diyl)magnesium complex;
   (c) contacting the (2-butene-1,4-diyl)magnesium complex with an imine to form a 1,2-addition adduct of the (2-butene-1,4-diyl)magnesium complex and imine;
   (d) contacting the 1,2-addition adduct with $CO_2$ at a temperature of about −78° C. to about 30° C. to form a nucleophilic addition product;
   (e) contacting the nucleophilic addition product with an aqueous acid; and
   (f) warming the reaction mixture to a temperature greater than about 30° C. to form a γ-lactam.

18. A method for the preparation of an amine comprising:
   (a) contacting a magnesium(II) salt in an ethereal, polyethereal, or hydrocarbon solvent with reducing agent having a reduction potential of about −1.5 volts, or more negative, relative to SCE, to form a highly reactive magnesium species;
   (b) contacting the highly reactive magnesium species with a conjugated diene, to form a (2-butene-1,4-diyl)magnesium complex;
   (c) contacting the (2-butene-1,4-diyl)magnesium complex with an imine to form a 1,2-addition adduct of the (2-butene-1,4-diyl)magnesium complex and imine;
   (d) contacting the 1,2-addition adduct with an aqueous acid to form an amine.

19. A method for the preparation of an amino acid comprising:
   (a) contacting a magnesium(II) salt in an ethereal, polyethereal, or hydrocarbon solvent with reducing agent having a reduction potential of about −1.5 volts, or more negative, relative to SCE, to form a highly reactive magnesium species;
   (b) contacting the highly reactive magnesium species with a conjugated diene, to form a (2-butene-1,4-diyl)magnesium complex;
   (c) contacting the (2-butene-1,4-diyl)magnesium complex with an imine to form a 1,2-addition adduct of the (2-butene-1,4-diyl)magnesium complex and imine;

(d) contacting the 1,2-addition adduct with $CO_2$ at a temperature of about $-78°$ C. to about $30°$ C. to form a nucleophilic addition product; and (e) contacting the nucleophilic addition product with an aqueous acid at a temperature no greater than about $30°$ C. to form an amino acid.

20. A method for the preparation of alcohol comprising:

(a) contacting a magnesium(II) salt in an ethereal, polyethereal, or hydrocarbon solvent with reducing agent having a reduction potential of about $-1.5$ volts, or more negative, relative to SCE, to form a highly reactive magnesium species;

(b) contacting the highly reactive magnesium species with a conjugated diene, to form a (2-butene-1,4-diyl)magnesium complex;

(c) contacting the (2-butene-1,4-diyl)magnesium complex with an epoxide to form a 1,2-addition adduct of the (2-butene-1,4-diyl)magnesium complex; and (d) contacting the 1,2-addition adduct with an aqueous acid to form an alcohol.

21. The method of claim 20 wherein the epoxide is an unsymmetrical epoxide having a hydroxyl functional group and the alcohol formed is a vicinal diol.

22. The method of claim 21 wherein the unsymmetrical epoxide is a chiral epoxide and the vicinal diol formed is a chiral vicinal diol.

23. A method for preparation of a zerovalent magnesium species comprising contacting a Mg(II) salt in a nonhydroxylic solvent with a reducing agent having a reduction potential of about $-1.5$ volt or more negative relative to a standard calomel electrode; wherein the Mg(II) salt is selected from the group consisting of sulfate, nitrate, nitrite, and cyanide.

24. A zerovalent magnesium species prepared by the method of claim 23.

25. A method for preparation of a zerovalent highly reactive magnesium species comprising the steps of:

(a) contacting an alkali metal, in a nonhydroxylic solvent, with an effective catalytic amount of an electron transfer compound to form a solution of an alkali metal complex reducing agent containing unreacted alkali metal; and (b) adding a Mg(II) salt to the solution of the alkali metal complex reducing agent containing unreacted alkali metal, at a rate such that the alkali metal complex reducing agent is in excess relative to solubilized Mg(II) salt, to form a zerovalent highly reactive magnesium species.

26. A zerovalent highly reactive magnesium species prepared by the method of claim 25.

27. A method for preparation of a zerovalent magnesium species comprising the steps of:

(a) reducing an electron transfer compound electrochemically in an ethereal or polyethereal solvent in the presence of an alkali metal salt to form a solution of an alkali metal complex reducing agent; and (b) adding a Mg(II) salt to the solution of the alkali metal complex reducing agent to form a zerovalent magnesium species.

28. A zerovalent magnesium species prepared by the method of claim 27.

* * * * *

UNITED STATES PATENT AND TRADEMARK OFFICE
CERTIFICATE OF CORRECTION

PATENT NO. : 5,498,734
DATED : March 12, 1996
INVENTOR(S) : Reuben D. Dieke

It is certified that error appears in the above-indentified patent and that said Letters Patent is hereby corrected as shown below:

In Column 2, line 55, "carded" should read --carried--.

In Column 10, line 21, "carded" should read --carried--.

In Column 11, lines 13 and 51, "carded" should reac --carried--.

In Column 12, lines 21, 35 and 39, "carded" should read --carried--.

In Column 17, line 54, "carded" should read --carried--.

In Column 21, line 34, "carder" should read --carried--.

In Column 34, line 51, "carded" should read --carried--.

In Column 3, line 46, "aidehyde" should read --aldehyde--.

In Column 11, line 44 two times, "aidehyde" should read --aldehyde--.

In Column 6, line 60, "carder" should read --carrier--.

In Column 11, line 55, "$(-COO^{31})$" should read --$(-COO^-)$--.

In Column 13, lines 10 and 11, "allylie" should read --allylic--.

UNITED STATES PATENT AND TRADEMARK OFFICE
CERTIFICATE OF CORRECTION

PATENT NO. : 5,498,734
DATED : March 12, 1996
INVENTOR(S) : Reuben D. Dieke

It is certified that error appears in the above-indentified patent and that said Letters Patent is hereby corrected as shown below:

In Column 17, line 42, "heterocyle" should read --heterocycle--.

In Column 17, line 44, "$C_{1-C100}$" should read --$C_1$-$C_{100}$--.

In Column 24, line 40, "$H_3^+$to" should read --$H_3O^+$ to--.

In Table II, Column 25, line 7, insert --1-- before the formula.
In Table III, Column 27, line 14, "CHCOOEt" should read --$CH_2COOEt$--.

In Column 29, line 37 and 45, "stiffed" should read --stirred--.

In Column 31, line 35 "3-oxaspir" should read --3-oxaspiro--.

In Column 39, line 2, "trimethylsilymethyl" should read --trimethylsilylmethyl--.

Signed and Sealed this

Eighth Day of October, 1996

Attest:

BRUCE LEHMAN

Attesting Officer   Commissioner of Patents and Trademarks